(12) United States Patent
Melancon et al.

(10) Patent No.: US 10,010,558 B2
(45) Date of Patent: Jul. 3, 2018

(54) FRANKIAMICIN A COMPOSITIONS AND METHODS

(71) Applicants: STC.UNM, Albuquerque, NM (US); Charles Melancon, Albuquerque, NM (US); Pamela Hall, Albuquerque, NM (US); Jacob Greenberg, Albuquerque, NM (US); Yasushi Ogasawara, Hokkaido (JP); Snezna Rogelj, Socorro, NM (US)

(72) Inventors: Charles Melancon, Albuquerque, NM (US); Pamela Hall, Albuquerque, NM (US); Jacob Greenberg, Albuquerque, NM (US); Yasushi Ogasawara, Sapporo (JP); Snezna Rogelj, Socorro, NM (US)

(*) Notice: Subject to any disclaimer, the term of this patent is extended or adjusted under 35 U.S.C. 154(b) by 0 days.

(21) Appl. No.: 15/552,541

(22) PCT Filed: Feb. 23, 2016

(86) PCT No.: PCT/US2016/019092
§ 371 (c)(1),
(2) Date: Aug. 22, 2017

(87) PCT Pub. No.: WO2016/137968
PCT Pub. Date: Sep. 1, 2016

(65) Prior Publication Data
US 2018/0050050 A1  Feb. 22, 2018

Related U.S. Application Data

(60) Provisional application No. 62/119,601, filed on Feb. 23, 2015.

(51) Int. Cl.
*A61K 31/65* (2006.01)

(52) U.S. Cl.
CPC .................... *A61K 31/65* (2013.01)

(58) Field of Classification Search
None
See application file for complete search history.

(56) References Cited

PUBLICATIONS

Udwary et al., Applied and Environmental Microbiology (2011), 77(11), pp. 3617-3625.*
Furumai et al., The Journal of Antibiotics (1993), 46(3), pp. 412-419.*
Tsuno et al., The Journal of Antibiotics (1993), 46(3), pp. 420-429.*
Kakinuma et al., The Journal of Antibiotics (1993), 46(3), pp. 43-440.*
Akiva et al., "The structure-function linkage database" 2014 *Nucleic Acids Res* vol. 42: pp. D521-530.
Altschul et al., "Basic local alignment search tool" 1990 *J Mol Biol* vol. 215: pp. 403-410.
Ames et al., "Crystal structure and functional analysis of tetracenomycin ARO/CYC: implications for cyclization specificity of aromatic polyketides" 2008 *Proc Nat Acad Sci USA* vol. 105: pp. 5349-5354.
Aoyama et al., "Bequinostatins A and B new inhibitors of glutathione S-transferase, produced by *Streptomyces* sp. MI384-DF12. Production, isolation, structure determination and biological activities" 1993 *J Antibiot* vol. 46: pp. 914-920.
Banskota et al., "TLN-05220, TLN-05223, new echinosporamicin-type antibiotics, and proposed revision of the structure of bravomicins" 2009 *J Antibiot* vol. 62: pp. 565-570.
Bao et al., "Reconstitution of the iterative type II polyketide synthase for tetracenomycin F2 biosynthesis" 1998 *Biochemistry* vol. 37: pp. 8132-8138.
Benson et al., "The biology of *Frankia* sp. Strains in the post-genome era" 2011 *Mol Plant Microbe Interact* vol. 24: pp. 1310-1316.
Bentley et al., "Complete genome sequence of the model actinomycete *Streptomyces coelicolor* A3 (2)" 2002 *Nature* vol. 417: pp. 141-147.
Blin et al., "antiSMASH 2.0—a versatile platform for genome mining of secondary metabolites" 2013 *Nucleic Acids Res* vol. 41: pp. W204-212.
Bologa et al., "Emerging trends in the discovery of natural product antibacterials" 2013 *Curr Opin Pharmacol* vol. 13: pp. 678-687.
Chen et al., "Role and regulation of bacterial LuxR-like regulators" 2011 *J Cell Biochem* vol. 112: pp. 2694-2702.
Chung et al., "Expression, purification, and characterization of AknX anthrone oxygenase, which is involved in aklavinone biosynthesis in *Streptomyces galilaeus*" 2002 *J Bacteriol* vol. 184: pp. 6115-6122.
Crawford et al., "New insights into the formation of fungal aromatic polyketides" 2010 *Nat Rev Microbiol* vol. 8: pp. 879-889.
Dairi et al., "Cloning and nucleotide sequence of the putative polyketide synthase genes for pradimicin biosynthesis from *Actinomadura hibisca*" 1997 *Biosci Biotechnol Biochem* vol. 61: pp. 1445-1453.
Feng et al., "Environmental DNA-encoded antibiotics fasamycins A and B inhibit FabF in type II fatty acid biosynthesis" 2012 *J Am Chem Soc* vol. 134: pp. 2981-2987.
Fritzsche et al., "Orchestration of discoid polyketide cyclization in the resistomycin pathway" 2008 *J Am Chem Soc* vol. 130: pp. 8307-8316.
Frolova et al., "Exploring natural product chemistry and biology with multicomponent reactions. 5. Discovery of a novel tubulin-targeting scaffold derived from the rigidin family of marine alkaloids" 2013 *J Med Chem* vol. 56: pp. 6886-6900.

(Continued)

*Primary Examiner* — Brian J Davis
(74) *Attorney, Agent, or Firm* — Mueting, Raasch & Gebhardt, P.A.

(57) ABSTRACT

In one aspect, this disclosure describes a pharmaceutical composition that generally includes frankiamicin A and a pharmaceutically acceptable carrier. In another aspect, this disclosure describes a method of treating a subject having, or at risk of having, a condition caused by a microbial infection treatable with frankiamicin A. Generally, the method includes administering to the subject an amount of frankiamicin A effective to ameliorate at least one symptom or clinical sign of the condition.

5 Claims, 18 Drawing Sheets

(56) References Cited

PUBLICATIONS

Grocholski et al., "Crystal structure of the cofactor-independent monooxygenase SnoaB from *Streptomyces nogalater*: implications for the reaction mechanism" 2010 *Biochemistry* vol. 49: pp. 934-944.

Helfrich et al., "Recent advances in genome-based polyketide discovery" 2014 *Curr Opin Biotechnol* vol. 29: 107-115.

Hertweck et al., "Context-dependent behavior of the enterocin iterative polyketide synthase; a new model for ketoreduction," 2004 *Chem Biol* vol. 11: pp. 461-468.

Hertweck et al., "Type II polyketide synthases: gaining deeper insight into enzymatic teamwork" 2007 *Nat Prod Rep* vol. 24: pp. 162-190.

Hutchinson, "Biosynthetic studies of daunorubicin and tetracenomycin" 1997 *Chem Rev* vol. 97: pp. 2525-2535.

Ishida et al., "Induced biosynthesis of cryptic polyketide metabolites in a *Burkholderia thailandensis* quorum sensing mutant" 2010 *J Am Chem Soc* vol. 132: pp. 13966-13968.

Kang et al., "Arixanthomycins A-C: Phylogeny-guided discovery of biologically active eDNA-derived pentangular polyphenols" 2014 *ACS Chem Biol* vol. 9: pp. 1267-1272.

Keating-Clay et al., "An antibiotic factory caught in action" 2004 *Nat Struct Mol Biol* vol. 11: pp. 888-893.

Kendrew et al., "Identification of a monooxygenase from *Streptomyces coelicolor* A3(2) involved in biosynthesis of actinorhodin: purification and characterization of the recombinant enzyme" 1997 *J Bacteriol* vol. 179: pp. 4305-4310.

Kim et al., "Cloning, sequencing, and characterization of the pradimicin biosynthetic gene cluster of *Actinomadura hibisca*" 2007 *J Microbiol Biotechnol* vol. 17: pp. 830-839.

Kim et al., "PKMiner: a database for exploring type II polyketide synthases" 2012 *BMC Microbiol*. vol. 12: p. 169.

Klika et al., "Frankiamide, a highly unusual macrocycle containing the imide and orthoamide functionalities from the symbiotic actinomycete *Frankia*" 2001 *J Org Chem* vol. 66: 4065-4068.

Komatsu et al., "Proteins encoded by the conservon of *Streptomyces coelicolor* A3(2) comprise a membrane-associated heterocomplex that resembles eukaryotic G protein-coupled regulatory system" 2006 *Mol Microbiol* vol. 62: pp. 1534-1546.

Kudo et al., "Cloning of the biosynthetic gene cluster for naphthoxanthene antibiotic FD-594 from *Streptomyces* sp. TA-0256" 2011 *J Antibiot* vol. 64: pp. 123-132.

Lackner et al., "Biosynthesis of pentangular polyphenols: deductions from the benastatin and griseorhodin pathways" 2007 *J Am Chem Soc* vol. 129: pp. 9306-9312.

Laureti et al., "Identification of a bioactive 51-membered macrolide complex by activation of a silent polyketide synthase in *Streptomyces ambofaciens*" 2011 *Proc Nat Acad Sci USA* vol. 108: pp. 6258-6263.

Lechner et al., "Selective overproduction of the proteasome inhibitor salinosporamide A via precursor pathway regulation" 2011 *Chem Biol* vol. 18: pp. 1527-1536.

Letunic et al., "Interactive tree of life v2: online annotation and display of phylogenetic trees made easy" 2011 *Nucleic Acids Res* vol. 39: pp. W475-478.

Li et al., "A gene cluster from a marine *Streptomyces* encoding the biosynthesis of the aromatic spiroketal polyketide griseorhodin A" 2002 *Chem Biol* vol. 9: pp. 1017-1026.

Li et al., "Automated genome mining for natural products" 2009 *BMC Bioinformatics* vol. 10: p. 185.

Lopez et al., "Isolation of the lysolipin gene cluster of *Streptomyces tendae* Tü 4042" 2010 *Gene* vol. 461: pp. 5-14.

Martin et al., "Collinone, a new recombinant angular polyketide antibiotic made by an engineered *Streptomyces* strain" 2001 J Antibiot vol. 54: pp. 239-249.

Matharu et al., "MCAT is not required for in vitro polyketide synthesis in a minimal actinorhodin polyketide synthase from *Streptomyces coelicolor*" 1998 *Chem Biol* vol. 5: pp. 699-711.

Matsuda et al., "KS-619-1, a new inhibitor of $Ca^{2+}$ and calmodulin-dependent cyclic nucleotide phosphodiesterase from *Streptomyces californicus*" 1998 *J Antibiot* vol. 40: pp. 1104-1110.

Mayer et al., "LanV, a bifunctional enzyme: aromatase and ketoreductase during landomycin A biosynthesis" 2005 *Chembiochem* vol. 6: pp. 2312-2315.

McDaniel et al., "Engineered biosynthesis of novel polyketides: analysis of TcmN function in tetracenomycin biosynthesis" 1995 *J Am Chem Soc* vol. 117: pp. 6805-6810.

McDaniel et al., "Engineered biosynthesis of novel polyketides: influence of a downstream enzyme on the catalytic specificity of a minimal aromatic polyketide synthase" 1994 *Proc Nat Acad Sci USA* vol. 91: pp. 11542-11546.

Metsa-Ketela et al., "Molecular evolution of aromatic polyketides and comparative sequence analysis of polyketide ketosynthase and 16S ribosomal DNA gene from various *Streptomyces* species" 2002 *Appl Environ Microbiol* vol. 68: pp. 4472-4479.

Napan et al., "A key cytochrome P450 hydroxylase in pradimicin biosynthesis" 2012 *Bioorg Med Chem Lett* vol. 22: pp. 606-609.

Normand et al., Genome characteristics of facultatively symbiotic *Frankia* sp. Strains reflect host range and plant biogeography 2007 *Genome Res* vol. 17: pp. 7-15.

Oves-Costales et al., "Mining Microbial Genomes for Metabolic Products of Cryptic Pathways. In: Genilloud O, Vicente F, editors. Drug Discovery from Natural Products" 2012 *Cambridge: Royal Society of Chemistry* pp. 140-158.

Price et al., "FastTree 2—Approximate maximum-likelihood trees for large alignments" 2010 *Plos One* vol. 5: p. e9490.

Rickards, "Revision of the structures of the benz[a]naphthacene quinone metabolites G-2N and G-2A from bacteria of the genus *Frankia*" 1989 *J Antibiot* vol. 42: 336-339.

Romero et al., "Antibiotics as signal molecules" 2011 *Chem Rev* vol. 111: pp. 5492-5500.

Scherlach et al., "Triggering cryptic natural product biosynthesis in microorganisms" 2009 *Org Biomol Chem* vol. 7: pp. 1753-1760.

Sciara et al., "The structure of ActVA-Orf6, a novel type of monooxygenase involved in actinorhodin biosynthesis" 2003 *EMBO J* vol 22: pp. 205-215.

Shen et al., "Tetracenomycin F1 monooxygenase: oxidation of a naphthacenone to a naphthacenequinone in the biosynthesis of tetracenomycin C in *Streptomyces glaucescens*" 1993 *Biochemistry* vol. 32: pp. 6656-6663.

Shen et al., "Tetracenomycin F2 cyclase: intramolecular aldol condensation in the biosynthesis of tetracenomycin C in *Streptomyces glaucescens*" 1993 *Biochemistry* vol. 32: pp. 11149-11154.

Sievers et al., "Fast, scalable generation of high-quality protein multiple sequence alignments using clustal omega" 2011 *Mol Syst Biol* vol. 7: pp. 539.

Tang et al., "Polyketide chain length control by chain length factor" 2003 *J Am Chem Soc* vol. 125: pp. 12708-12709.

Thompson et al., "Structural and functional analysis of tetracenomycin F2 cyclase from *Streptomyces glaucescens*. A type II polyketide cyclas" 2004 *J Biol Chem* vol. 279: pp. 37956-37963.

Walsh et al., "Natural products version 2.0: connecting genes to molecules" 2010 *J Am Chem Soc*, vol. 132: pp. 2469-2493.

Weber et al., "Clusean: a computer-based framework for the automated analysis of bacterial secondary metabolite biosynthetic gene clusters," 2009 *J Biotechnol* vol. 140: pp. 13-17.

Wendt-Pienkowski et al., "Cloning, sequencing, analysis, and heterologous expression of the fredericamycin biosynthetic gene cluster from *Streptomyces griseus*" 2005 *J Am Chem Soc* vol. 127: pp. 16442-16452.

Xu et al.,"Molecular analysis of the benastatin biosynthetic pathway and genetic engineering of altered fatty acid-polyketide hybrids" 2007 *J Am Chem Soc* vol. 129: pp. 6022-6030.

Yamanaka et al., "Direct cloning and refactoring of a silent lipopeptide biosynthetic gene cluster yields the antibiotic taromycin A" 2014 *Proc Nat Acad Sci USA* vol. 111: pp. 1957-1962.

Zaleta-Rivera et al., "Cloning, sequencing, heterologous expression, and mechanistic analysis of A-74528 biosynthesis" 2010 *J Am Chem Soc* vol. 132: pp. 9122-9128.

(56) References Cited

OTHER PUBLICATIONS

Zawada et al., "Heterologous expression, purification, reconstitution and kinetic analysis of an extended type II polyketide synthase" 1999 *Chem Biol* vol. 6: pp. 607-615.

Zhan et al., "Investigation of tailoring modifications in pradimicin biosynthesis" 2009 Chembiochem vol. 10: pp. 1447-1452.

Zhan et al., "Synergistic actions of a monooxygenase and cyclases in aromatic polyketide biosynthesis" 2008 *Chembiochem* vol. 9: pp. 1710-1715.

Zhang et al., "Biosynthetic investigations of lactonamycin and lactonamycin z: cloning of the biosynthetic gene clusters and discovery of an unusual starter unit" 2008 *Antimicrob Agents Chemother* vol. 52: pp. 574-585.

Zhang et al., "Unveiling the post-PKS redox tailoring steps in biosynthesis of the type II polyketide antitumor antibiotic xantholipin" 2012 *Chem Biol* vol. 19: pp. 422-432.

Zhao et al., "Prediction and characterization of enzymatic activities guided by sequence similarity and genome neighborhood networks" 2014 *Elife* vol. 3: p. e03275.

International Search Report and Written Opinion PCT/US2016/019092 dated Aug. 18, 2016.

International Preliminary Report on Patentability PCT/US2016/019092 dated Sep. 8, 2017.

\* cited by examiner

FIG. 1
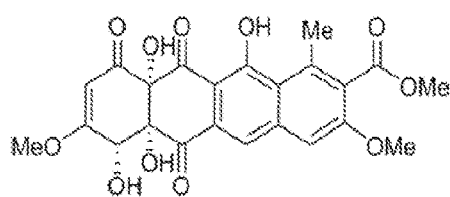
1
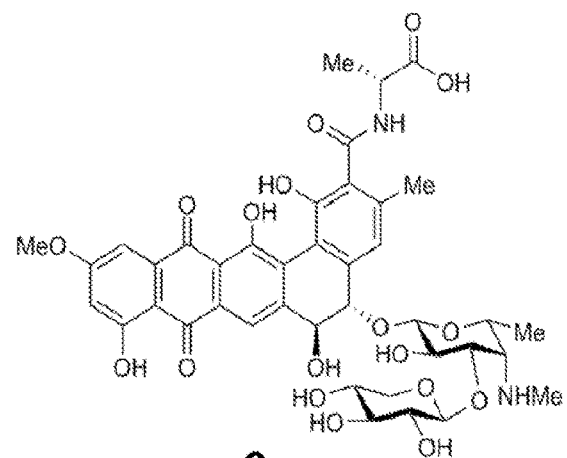
2
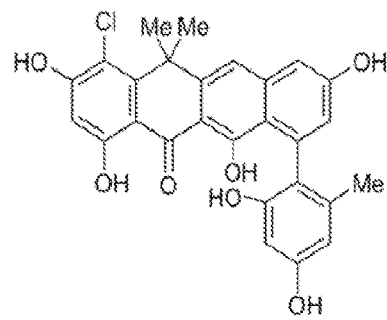
3
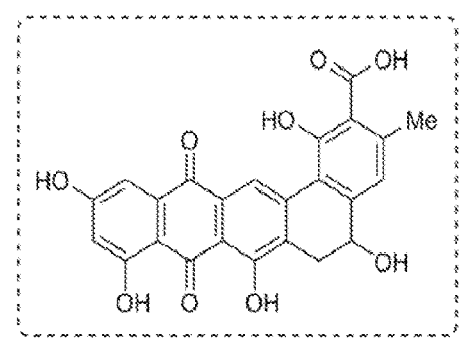
4

Frankiamicin A, 13C NMR, 75 MHz, DMSO-d6

Frankiamicin A, 1H–1H COSY, 500 MHz, DMSO–d6

Frankiamicin A, HMQC, 500 MHz, DMSO-$d_6$

Frankiamicin A, HMBC, 500 MHz, DMSO-$d_6$

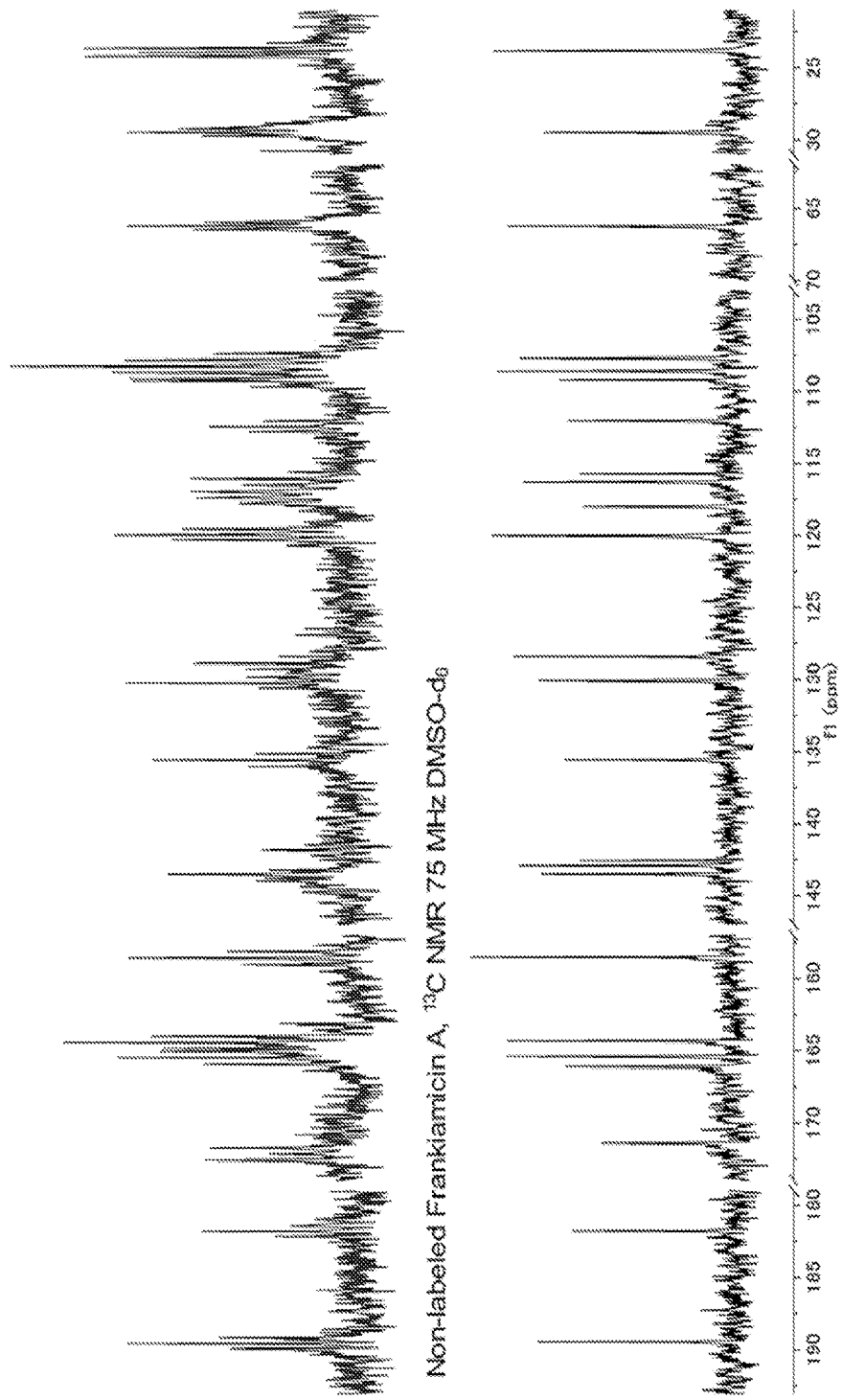

FRANKIAMICIN A COMPOSITIONS AND METHODS

CROSS-REFERENCE TO RELATED APPLICATION

This application is the § 371 U.S. National Stage of International Application No. PCT/US2016/019092, filed Feb. 23, 2016, which claims priority to U.S. Provisional Patent Application Ser. No. 62/119,601, filed Feb. 23, 2015, each of which is incorporated herein by reference.

SUMMARY

This disclosure describes, in one aspect, a pharmaceutical composition that generally includes frankiamicin A and a pharmaceutically acceptable carrier.

In another aspect, this disclosure describes a method of treating a subject having, or at risk of having, a condition caused by a microbial infection treatable with frankiamicin A. Generally, the method includes administering to the subject an amount of frankiamicin A effective to ameliorate at least one symptom or clinical sign of the condition.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 1. Structures of prototypical type II polyketides. Structures of chlortetracycline (1), doxorubicin (2), R1128A (3), and the pentangular polyketide frankiamicin A (4) identified in this study.

FIG. 16. Comparison of $^{13}$C spectra of unlabeled frankiamicin A (4) and frankiamicin obtained by feeding [1,2-$^{13}$C$_2$] acetate doped with unlabeled compound.

DETAILED DESCRIPTION OF ILLUSTRATIVE EMBODIMENTS

Figure 2:
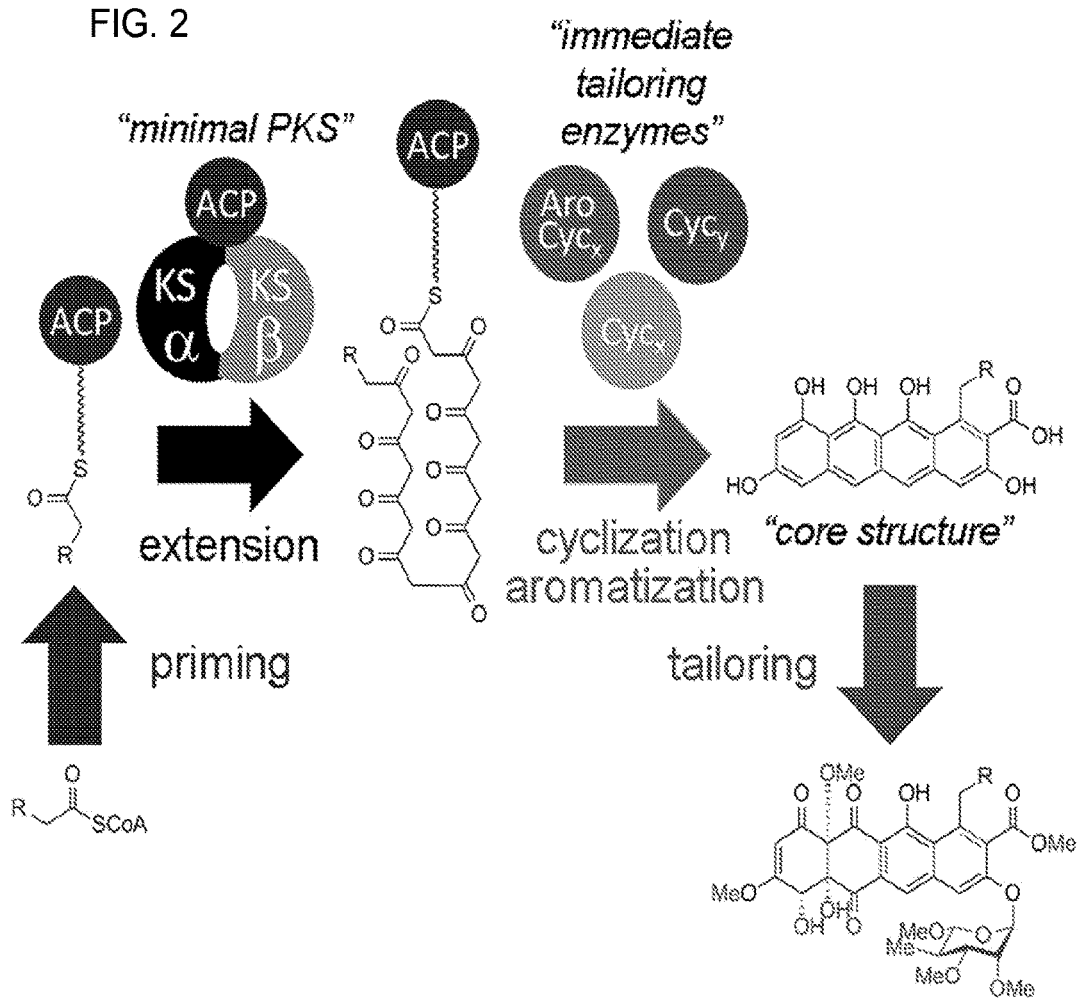
FIG. 2. General summary of type II polyketide biosynthesis. The key steps in type II polyketide biosynthesis—priming of the minimal polyketide synthase, extension of the polyketide chain by the ketosynthase α/β heterodimer to generate the poly-β-ketone intermediate, cyclization and aromatization of the poly-β-ketone by the immediate tailoring enzymes (aromatase/cyclase and cyclases) to form the cyclized core structure, and tailoring by various polyketide tailoring enzymes—are shown, using the elloramycin biosynthetic pathway as an example. Structural elements of the intermediates and final product are color-coded according to which enzymes catalyze their formation.

This disclosure describes a method that includes administering an effective amount of the composition to a subject having, or at risk of having, a condition caused by a microbial infection treatable with frankiamicin A. In this aspect of the invention, an "effective amount" is an amount effective to reduce, limit progression, ameliorate, or resolve, to any extent, the symptoms or clinical signs related to the condition.

Frankiamicin A may be formulated into a composition along with a pharmaceutically acceptable carrier. As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the active ingredient, its use in the therapeutic compositions is contemplated. Supplementary active ingredients also can be incorporated into the compositions. As used herein, "pharmaceutically acceptable" refers to a material that is not biologically or otherwise undesirable, i.e., the material may be administered to an individual along with frankiamicin A without causing any undesirable biological effects or interacting in a deleterious manner with any of the other components of the pharmaceutical composition in which it is contained.

Thus, frankiamicin A may be formulated into a pharmaceutical composition. The pharmaceutical composition may be formulated in a variety of forms adapted to a preferred route of administration. Thus, a composition can be administered via known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). A pharmaceutical composition containing frankiamicin A also can be administered via a sustained or delayed release.

A formulation may be conveniently presented in unit dosage form and may be prepared by methods well known in the art of pharmacy. Methods of preparing a composition with a pharmaceutically acceptable carrier include the step of bringing frankiamicin A into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

A pharmaceutical composition containing frankiamicin A may be provided in any suitable form including but not limited to a solution, a suspension, an emulsion, a spray, an aerosol, or any form of mixture. The composition may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, and the like. The formulation may further include one or more additives including such as, for example, an adjuvant, a skin penetration enhancer, a colorant, a fragrance, a flavoring, a moisturizer, a thickener, and the like.

The amount of frankiamicin A administered can vary depending on various factors including, but not limited to, the microbe for which frankiamicin A is being administered, the weight, physical condition, and/or age of the subject, and/or the route of administration. Thus, it is not practical to set forth generally the amount that constitutes an amount of frankiamicin A effective for all possible applications. Those of ordinary skill in the art, however, can readily determine the appropriate amount with due consideration of such factors.

In some embodiments, the method can include administering sufficient frankiamicin A to provide a dose of, for example, from about 100 ng/kg to about 50 mg/kg to the subject, although in some embodiments the methods may be performed by administering frankiamicin A in a dose outside this range. In some of these embodiments, the method includes administering sufficient frankiamicin A to provide a dose of from about 10 μg/kg to about 5 mg/kg to the subject, for example, a dose of from about 100 μg/kg to about 1 mg/kg.

Alternatively, the dose may be calculated using actual body weight obtained just prior to the beginning of a treatment course. For the dosages calculated in this way, body surface area (m$^2$) is calculated prior to the beginning of the treatment course using the Dubois method: m$^2$=(wt kg$^{0.425}$×height cm$^{0.725}$)×0.007184.

In some embodiments, the method can include administering sufficient frankiamicin A to provide a dose of, for example, from about 0.01 mg/m$^2$ to about 10 mg/m$^2$.

In some embodiments, frankiamicin A may be administered, for example, from a single dose to multiple doses per week, although in some embodiments the method can be performed by administering frankiamicin A at a frequency outside this range. In certain embodiments, frankiamicin A may be administered once per day. In other embodiments, frankiamicin A may be provided on an as needed basis. In still other embodiments, frankiamicin A may be provided on a continuous basis while a subject has, or is at risk of having, a microbial infection treatable with frankiamicin A.

Thus, frankiamicin A may be administered prophylactically (i.e., before a subject manifests any symptoms or clinical signs of infection by a microbe treatable with frankiamicin A) or, alternatively, can be initiated after the subject exhibits one or more symptoms or clinical signs of the condition. Frankiamicin A may be prophylactically administered to a subject that is at risk of a microbial infection treatable with frankiamicin A—while an infection or colonization remains subclinical. As used herein, the term "at risk" refers to a subject that may or may not actually possess the described risk. Thus, for example, a subject "at risk" of an infectious condition is a subject present in an area where other individuals have been identified as having the infectious condition and/or is likely to be exposed to the infectious agent even if the subject has not yet manifested any detectable indication of infection by the microbe and regardless of whether the subject may harbor a subclinical amount of the microbe. Accordingly, administration of a pharmaceutical composition containing frankiamicin A can be performed before, during, or after the subject first exhibits a symptom or clinical sign of the condition.

The advent of high-throughput, low-cost bacterial genome sequencing allows one to study previously unstudied natural product biosynthetic gene clusters from diverse and unstudied organisms. The volume of unstudied organisms is so great that they cannot all be studied using traditional experimental approaches. Global bioinformatic and comparative genomic analysis facilitates more complete and integrated use of this large volume of sequence data, together with the existing experimentally-derived knowledge base, to select for experimental characterization specific gene clusters with atypical sequence characteristics. The results of such bioinformatics-guided characterization endeavors can illuminate links between gene clusters and the molecules they produce that can lead to a more detailed understanding of gene cluster sequence/function relationships within an entire class of natural products; and can serve as a solid foundation for generating additional biosynthetic hypotheses.

Such a global bioinformatic/comparative genomic approach was applied to bacterial type II polyketide gene clusters. A subset of these clusters revealed a clade of unstudied *Frankia* KSα/β enzymes that possess divergent sequence characteristics. These gene clusters biosynthesize a product with a core structure made from a poly-β-ketone intermediate of at least 24 carbons; and that the core structure undergoes minimal tailoring modifications. Identification, isolation, and structure elucidation of the compound produced by a representative of this class of gene clusters from *Frankia* sp. EAN1pec revealed that the cluster biosynthesizes the 24-carbon pentangular type II polyketide (4), establishing the product specificity of the KSα/β and demonstrating the collective function of the cyclases.

Polyketides are a structurally diverse family of natural products known for their medicinally useful bioactivities as well as for their ecological roles. Among these, members of the bacterial type II polyketide class, exemplified by the antitumor agent tetracenomycin C (1), the antifungal pradimicin A (2), and the antibacterial compound fasamycin A (3) are characterized by planar aromatic fused ring core structures and a common biosynthetic origin (FIG. 1).

In bacterial type II polyketide biosynthesis, the ketosynthase α/β/acyl carrier protein (KSα/β/ACP) "minimal polyketide synthase" complex is responsible for iterative Claisen condensation of an ACP-bound starter unit and a specific number of malonyl-CoA-derived acetate extender units to generate a poly-β-ketone chain of defined length. These poly-β-ketone intermediates then undergo a series of regiospecific "immediate tailoring" reactions—i.e., optional C-9 ketoreduction, cyclizations, and aromatizations—to form planar aromatic "core structures", the first stable pathway intermediates. These core structures are then elaborated by myriad tailoring enzymes, including oxygenases, methyltransferases, reductases, and glycosyltransferases (FIG. 2).

The KSα/β heterodimer controls the chain length of the poly-β-ketone intermediate, with 16- to 30-carbon chains known thus far. The size and shape of the KSα/β active site may control the length of the poly-β-ketone produced. Cyclization and dehydration reactions are catalyzed by specific sets of three to four cyclases to form particular planar aromatic core structures characteristic of each type II polyketide structural subclass.

The genetic capacity to produce natural products, including bacterial type II polyketides, is widespread, and extends to many bacterial genera that are unexploited or underexploited with respect to natural products. The existence of a vast untapped reservoir of natural product gene clusters in microbial genome sequences underscores the need for systematic, combined bioinformatic/experimental approaches to more completely understand natural product gene and gene cluster sequence/function relationships and to more efficiently link gene clusters with the compounds they produce. Application of such approaches will, over time, expand and organize the collective knowledge base on natural product biosynthesis, allowing increasingly rapid, accurate, and large-scale prediction, elucidation, and bioengineering of natural product pathways and compound structures from gene cluster sequences. Similar approaches have been successfully applied to studying sequence/function relationships in enzyme superfamilies and for operons involved in primary metabolism in microbes.

Bioinformatic analysis has begun to play an increasingly prominent role in natural product discovery and biosynthesis studies. A number of bioinformatics software packages such as antiSMASH (Blin et al., 2013, *Nucleic Acids Res* 41:W204-212), NP.searcher (Li et al., 2009, *BMC Bioinformatics* 10:185), and CLUSEAN (Weber et al., 2009, *J Biotechnol* 140:13-17) have been developed to automatically identify, annotate, and classify natural product gene clusters and to predict product structures given user-input DNA or protein sequences. Such software packages greatly facilitate annotation of individual newly-sequenced gene clusters and identification and classification of gene clusters from whole genome sequencing projects. However, the limited ability of these software packages to perform database-wide comparative gene and gene cluster analyses limits their utility for systematic study of sequence/function relationships. For such studies it is desirable to be able to globally survey all natural product gene clusters representing a particular biosynthetic class and select for experimental characterization clusters that are representative of groups with unique gene sequence characteristics or unique gene compositions. Some currently available software packages are also unable to identify bacterial type II polyketide gene clusters, and none are able to predict which structural subclass a type II polyketide gene cluster produces. PKMiner (Kim et al., 2012, *BMC Microbiol* 12:169), a database of 40 unstudied type II polyketide gene clusters from sequenced bacterial genomes, which includes structural subclass predictions, was recently reported. However, the PKMiner database must be manually updated, is incomplete, and lacks the necessary features to conduct global comparative analysis of bacterial type II polyketide genes and gene clusters.

This disclosure describes global identification and annotation of all bacterial type II polyketide gene clusters present in the NCBI databank and provides predictive information on compound structures produced by these clusters using the natural product bioinformatics software package DYNAMITE (Ogasawara et al., 2015, PLoS ONE 10(4): e0121505). DYNAMITE has unique capabilities beyond those of currently available software packages that facilitate global comparative analysis of natural product gene clusters (see EXAMPLES, bioinformatic analysis subsection for details).

To correlate training set ketosynthase α/β (KSα/β) sequences with poly-β-ketone chain lengths and to explore the possibility of predicting poly-β-ketone structures from KSα/β sequences, dendrogramatic analysis was performed on all ketosynthase α/β (KSα/β) sequences within these gene clusters. This analysis revealed strong correlations between the positions of KSα/β sequences in the dendrogram and both poly-β-ketone structure and structural subclass for training set members.

KSα/β dendrogramatic analysis revealed a clade of KSα/β sequences found exclusively in unstudied gene clusters, most of which occur in the genomes of *Frankia* species, whose sequences were sufficiently diverged from studied systems that the product poly-β-ketone chain lengths could not be predicted. Further comparative analysis of remaining biosynthetic genes in the *Frankia* clusters revealed strong gene synteny among the clusters and high similarity of encoded proteins to immediate tailoring enzymes involved in biosynthesis of type II polyketides from the pentangular and tetracenomycin subclasses.

To determine the polyketide chain length produced by this KSα/β clade and the structure of the product made by these gene clusters, extracts from three *Frankia* species harboring the cluster were screened to identify and structurally characterize the compound. Among the three strains, *Frankia* sp. EAN1pec, alone, produced a compound with spectral characteristics consistent with those of the predicted type II polyketide. Isolation and structure elucidation of the compound revealed it to be the pentangular type II polyketide 4, which was named frankiamicin A (FIG. 1), thereby revealing that the KSα/β is a member of a new 24 carbon poly-β-ketone-producing clade.

Bioinformatic Analysis

The bioinformatic software package DYNAMITE (Ogasawara et al., 2015, PLoS ONE 10(4): e0121505) can globally identify and annotate gene clusters responsible for producing three of the most common types of natural products—type I and type II polyketides and non-ribosomal peptides—in all sequences deposited in the NCBI databank to date, rather than in a specific input sequence. Global analysis using DYNAMITE allows one to circumscribe all bacterial type II polyketide biosynthetic gene clusters sequenced to date and to systematically compare protein sequences of homologues and distributions of homologous genes across type II polyketide gene clusters in search of proteins and gene clusters with atypical features.

Figure 3:
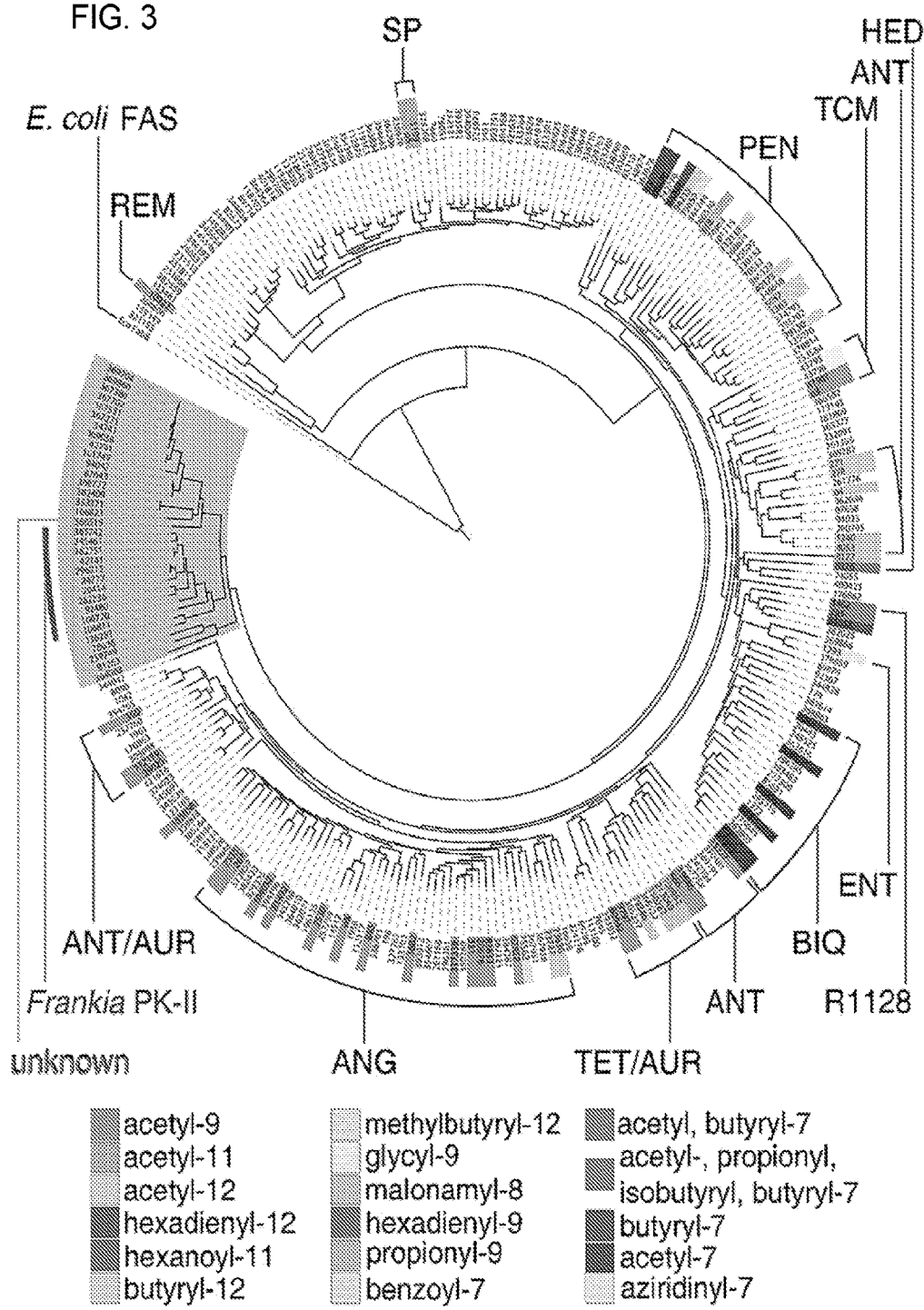
FIG. 3. Dendrogram of KSα/β sequences showing the relationship between dendrogramatic position, polyketide subclass, and poly-3-ketone structure. Dendrogram based on multiple alignment of 296 concatenated KSα/β protein sequences illustrating the large uncharacterized clade (left, shaded purple) in which KSα/β pairs from Frankia type II polyketide clusters that are the subject of this study (marked with purple bar) are found. KSα/β pairs from previously characterized type II polyketide clusters are colored according to their starter unit and number of extender units (see bottom figure legend, starter/extender colors are listed clockwise as they first appear in the figure). Type II polyketide subclasses are labeled and bracketed. Subclass abbreviations: REM—resistomycin; SP—spore pigment; PEN—pentangular; TCM—tetracenomycin; ANT—anthracycline; HED—hedamycin; R1128—R1128; ENT—enterocin; BIQ—benzoisochromanequinone; TET—tetracycline; AUR—aureolic acid; ANG—angucycline. Other abbreviations: E. coli FAS—E. coli fatty acid synthase, which was used as the outgroup.
Figure 4:
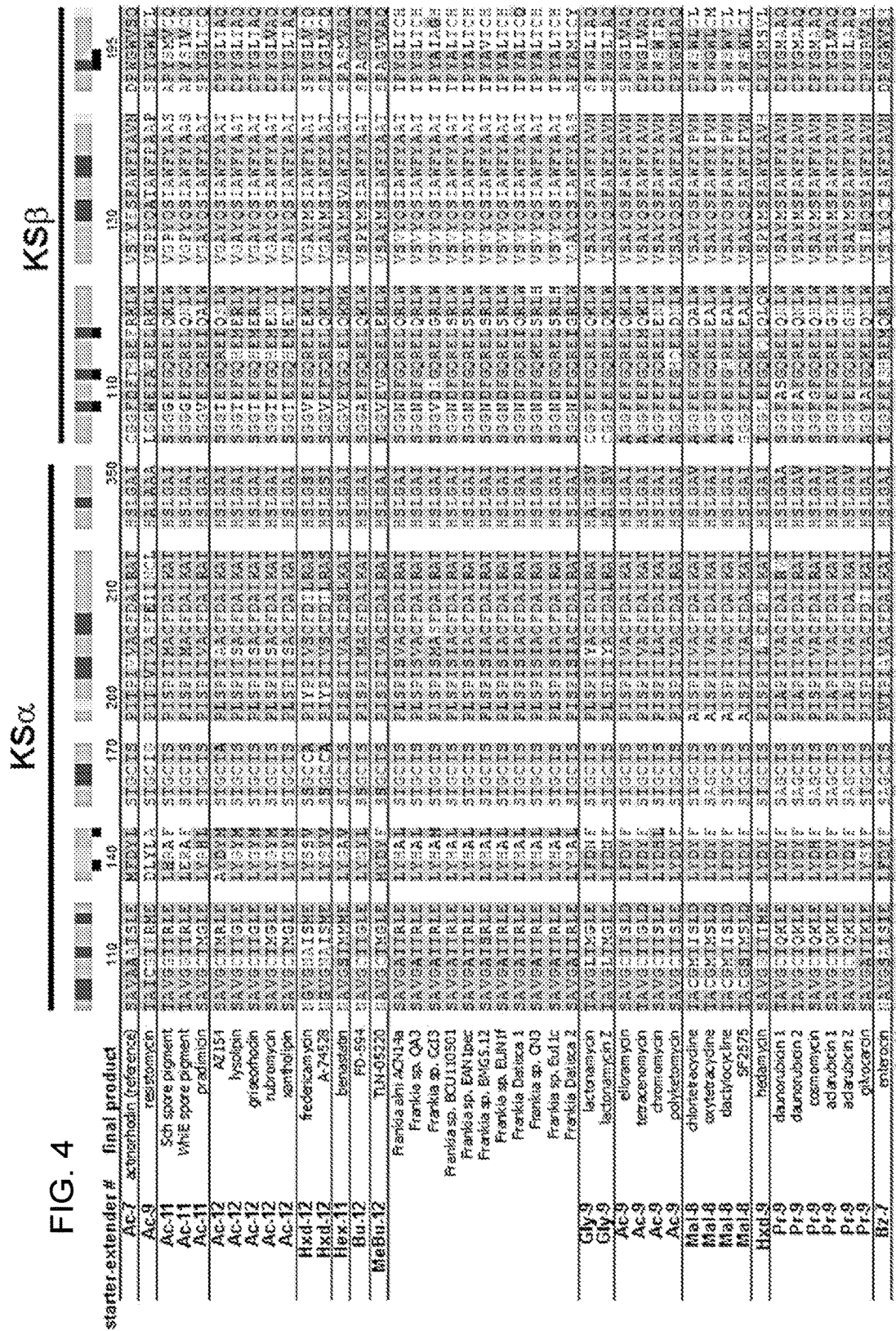
FIG. 4. Multiple sequence alignment of training set and Frankia KSα/β active site residues. Eight regions of KSα/β protein sequence from the 64 KSα/β training set members and eleven Frankia KSα/β sequences that are predicted to be in the closest proximity to the active site based on the X-ray crystal structure of the actinorhodin (act) KSα/β are shown. The five regions that lie within KSα and the three that lie within KSβ are noted by labeled black bars at the top of the figure. Predicted proximity to the active site is shown as a heat map at the top of the figure (red residues line the active site pocket, orange residues are within 4 Å of the residues that line the active site, yellow residues are within 6 Å, and green residue are within 8 Å. Black squares immediately below the heat map mark the seven residues previously proposed to be responsible for product specificity. Residues are numbered using act numbering. Training set product names and Frankia cluster names are given to the left. Starter unit and number of extender units of training set systems appear on the far left. Ac: acetyl; Pr: propionyl; Mal: malonamyl; Gly: glycyl; Bu: butyryl; iBu: isobutyryl; Azd: aziridinyl; Hxd: hexadienyl; Hex: hexanoyl; MeBu: 2-methylbutyryl; Bz: benzoyl.
Figure 4:
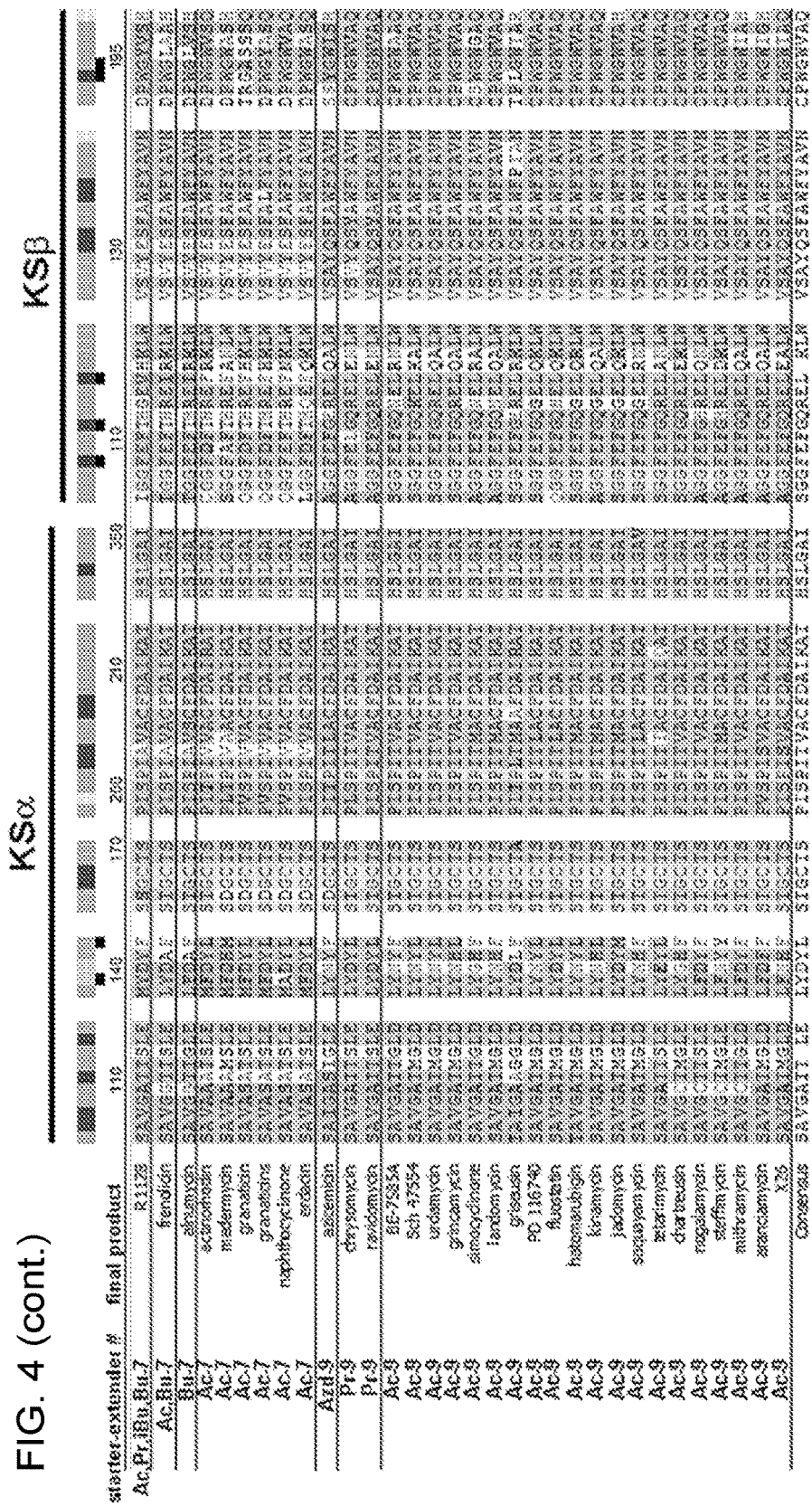
Figure 10:
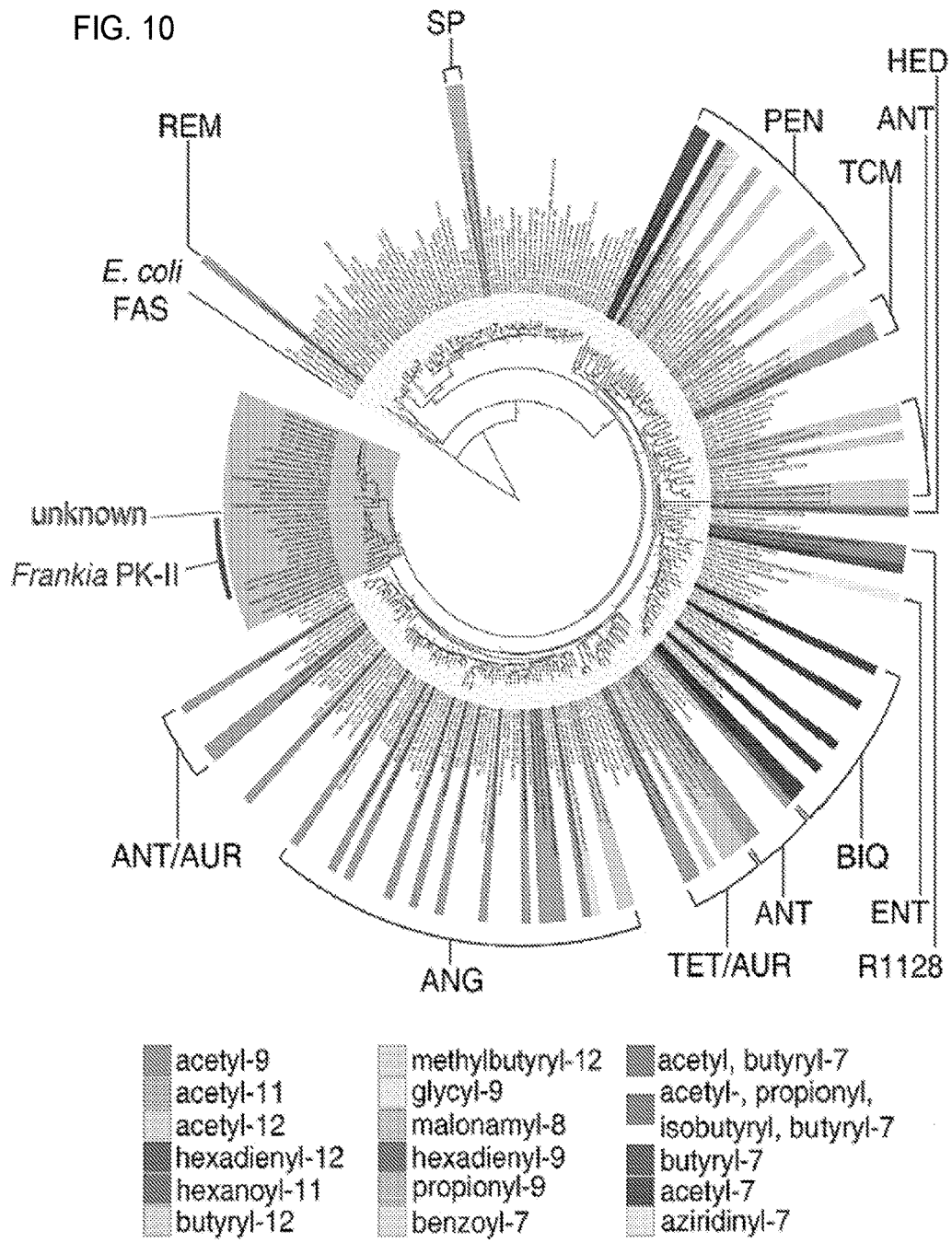
FIG. 10. High resolution version of the ketosynthase α/β dendrogram shown in FIG. 3 with bootstrap values.

After identifying all 296 putative bacterial type II polyketide gene clusters present in the NCBI databank as of December 2013, further comparative analyses of genes within these clusters was performed to identify those with unique sequence characteristics. Dendrogramatic analysis was performed on the sequences of KSα/β—the heterodimeric enzyme responsible for biosynthesis and chain length control of the poly-β-ketone precursors of all bacterial type II polyketides. FIG. 3 shows a dendrogram of concatenated KSα/β amino acid sequences from all 296 type II polyketide clusters identified by DYNAMITE (TABLE 4), including the 64 training set gene clusters responsible for biosynthesis of natural products with known poly-β-ketone lengths, structures, and cyclized core structures (FIG. 3, FIG. 10, colored by starter unit/extender unit number). This analysis revealed strong correlations between the positions of training set KSα/β sequences in the dendrogram and both poly-β-ketone chain length/structure and type II polyketide structural subclass. While most branches of the dendrogram harbor at least one training set KSα/β sequence, a large, diverged clade was identified that included only KSα/β sequences from uncharacterized type II polyketide gene clusters (FIG. 3, left, shaded). Within this clade were a closely related set of 11 KSα/β sequences from the genomes of 10 *Frankia* species (FIG. 3, marked with the bar), a group of nitrogen-fixing Actinobacterial plant root endophytes. *Frankia* genomes harbor a large and diverse set of polyketide and non-ribosomal peptide natural product gene clusters (see TABLE 5 and TABLE 6 for a list of all natural product gene clusters identified using DYNAMITE in the *Frankia* genomes analyzed, and for further information on these genomes). However, only three *Frankia* natural products—the related pentangular polyketides G-2A and G-2N and the calcium-binding antibiotic, demethyl cezomycin (frankiamide)—have been structurally characterized to date. Previously, crystal structure analysis of the actinorhodin KSα/β revealed amino acid residues of the enzyme active site, seven of which (F140, L143 of KSα and F109, T112, F116, W194, and G195 of KSβ) may be responsible for determining poly-β-ketone chain length, including three residues (F109, T112, F116 of KSβ) that had previously been shown through mutagenesis to be directly involved in chain length determination. In an attempt to gain further insight into the poly-β-ketone chain length produced by the *Frankia* KSα/β enzymes, the identities of the possible chain-length-determining amino acid residues and other residues in proximity to the active site of *Frankia* KSα/β were compared with those of all training set KSα/β via multiple sequence alignment. Overall, *Frankia* KSα/β active site residues were most similar to those of training set members producing poly-β-ketone intermediates of at least 24 carbons, particularly at positions 133, 139, and 140 of KSβ, where all training set sequences responsible for making products of at least 24 carbons had UV, A, S/T, respectively (FIG. 4). However there were some notable exceptions, such as the unique and well-conserved A110 and S204 of KSα and N109, D110, R118, V129, T192, A195 of KSβ.

Because of the distinct sequence characteristics of members of this clade and the lack of KSα/β sequences from the training set within the clade, it was not possible to predict with certainty from KSα/β sequence analysis which poly-β-ketone chain length/structure was produced by these enzymes, or the structural subclass to which their cyclized products belong.

Figure 5:
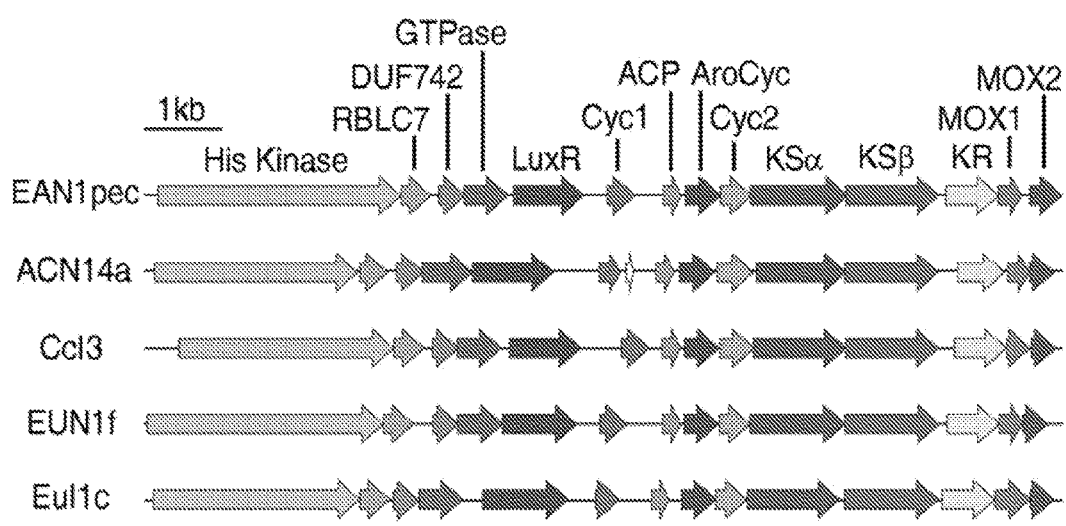
FIG. 5. Gene synteny in representative Frankia type II polyketide gene clusters. Homologous genes appear in the same color. Species abbreviations: EAN1pec: Frankia sp. EAN1pec; ACN14a: Frankia alni ACN14a; CcI3: Frankia sp. CcI3; EUN1f: Frankia sp. EUN1f; EuI1c: Frankia sp. EuI1c. Gene function abbreviations: His Kinase: histidine kinase; RBLC7: road block LC7 family protein; DUF742: domain of unknown function 742; GTPase: Ras family GTPase; LuxR: LuxR family transcriptional regulator; Cyc1: TcmI-like polyketide cyclase, AroCyc: TcmN-like aromatase/cyclase, Cyc2: TcmJ-like polyketide cyclase, KR: ketoreductase; MOX1: PdmH-like putative monooxygenase, MOX2: PdmI-like putative monooxygenase.

DYNAMITE analysis of the proteins encoded by genes adjacent to the *Frankia* KSα/β genes revealed seven other proteins characteristic of bacterial type II polyketide biosynthesis: an acyl carrier protein (ACP), three cyclases, two putative monooxygenases, and a ketoreductase. The DYNAMITE analysis also identified five proteins with homology to those involved in signal transduction and regulation of gene expression. Those five proteins exhibit nearly complete synteny and a high degree of sequence similarity (FIG. 5), suggesting that the clusters make the same or highly similar products. All 14 genes in each cluster are also co-directional, suggesting that they form a single operon. No additional conserved proteins with homology to known natural product biosynthetic or regulatory proteins were found encoded in the regions flanking these *Frankia* type II polyketide gene clusters.

Sequence comparison of each putative biosynthetic protein in the *Frankia* clusters to proteins from type II polyketide training set clusters revealed a high degree of similarity between each putative *Frankia* biosynthetic protein and proteins from pentangular and tetracenomycin subclass products (summarized in TABLE 7), suggesting that the *Frankia* clusters either produce a compound from one of these subclasses or form a novel, but biosynthetically closely related, subclass. The conserved set of three cyclases characteristic of pentangular and tetracenomycin subclass products—a monodomain aromatase/cyclase homologous to the N-terminal domain of TcmN, a cyclase with predicted cupin-like fold homologous to TcmJ, and a cyclase with predicted ferredoxin-like fold homologous to TcmI—were present in the clusters. Support for the tentative placement of the *Frankia* clusters within the pentangular subclass came from sequence analysis of the two putative monooxygenases and the ketoreductase found in each cluster. Homologues of each of the two putative monooxygenases are found encoded adjacent to each other in each pentangular training set cluster, whereas only a single more distantly related homologue is present in tetracenomycin subclass clusters; and the *Frankia* ketoreductases are highly similar to tailoring ketoreductases known to reduce the C-6 position of the polyketide in pentangular pathways, but are absent from tetracenomycin subclass clusters.

Biosynthesis of the polyketide core structures of seven of the sixteen pentangular, tetracenomycin, or related unique training set compounds are known or predicted to be initiated by incorporation of a non-acetate starter unit. In each case, a type III ketosynthase or stand-alone adenylation domain is present in the gene cluster. The absence of homologues of either of these genes in the *Frankia* cluster suggests that each produces an acetate-primed polyketide product.

In contrast to most training set type II polyketide clusters, which encode a number of additional tailoring enzymes, the *Frankia* clusters lack additional putative tailoring enzymes other than the ketoreductase, suggesting that their product represents a minimally modified aromatic polyketide.

Taken together, bioinformatic analysis suggests that the *Frankia* clusters in question biosynthesize a product made from an acetate primed poly-β-ketone of at least 24 carbons, are biosynthetically and structurally related to pentangular and tetracenomycin subclass compounds and are more similar to pentangular subclass compounds. However, the KSα/β sequences from these clusters have diverged sufficiently from those of training set members to preclude accurate chain length prediction. In order to establish a sequence-function relationship between this group of orphan gene clusters and their product, compounds made by this group of gene clusters were isolated and structurally characterized.

Chromatographic and Spectral Analysis of *Frankia* Extracts

Five *Frankia* strains (*Frankia alni* ACN14a, *Frankia* sp. CcI3, *Frankia* sp. EAN1pec, *Frankia* sp. EuI1c, and *Frankia* sp. EUN1f), each harboring a single copy of the gene cluster in question, were selected for characterization. Each was first grown in small scale in the recommended media (see EXAMPLES section, below). While the growth rates of all *Frankia* species examined were quite low (doubling of wet cell weight occurred every 2 to 3 weeks), those of *Frankia* sp. CcI3 and *Frankia* sp. EUN1f were the lowest. These two strains were therefore not pursued further.

Figure 6:
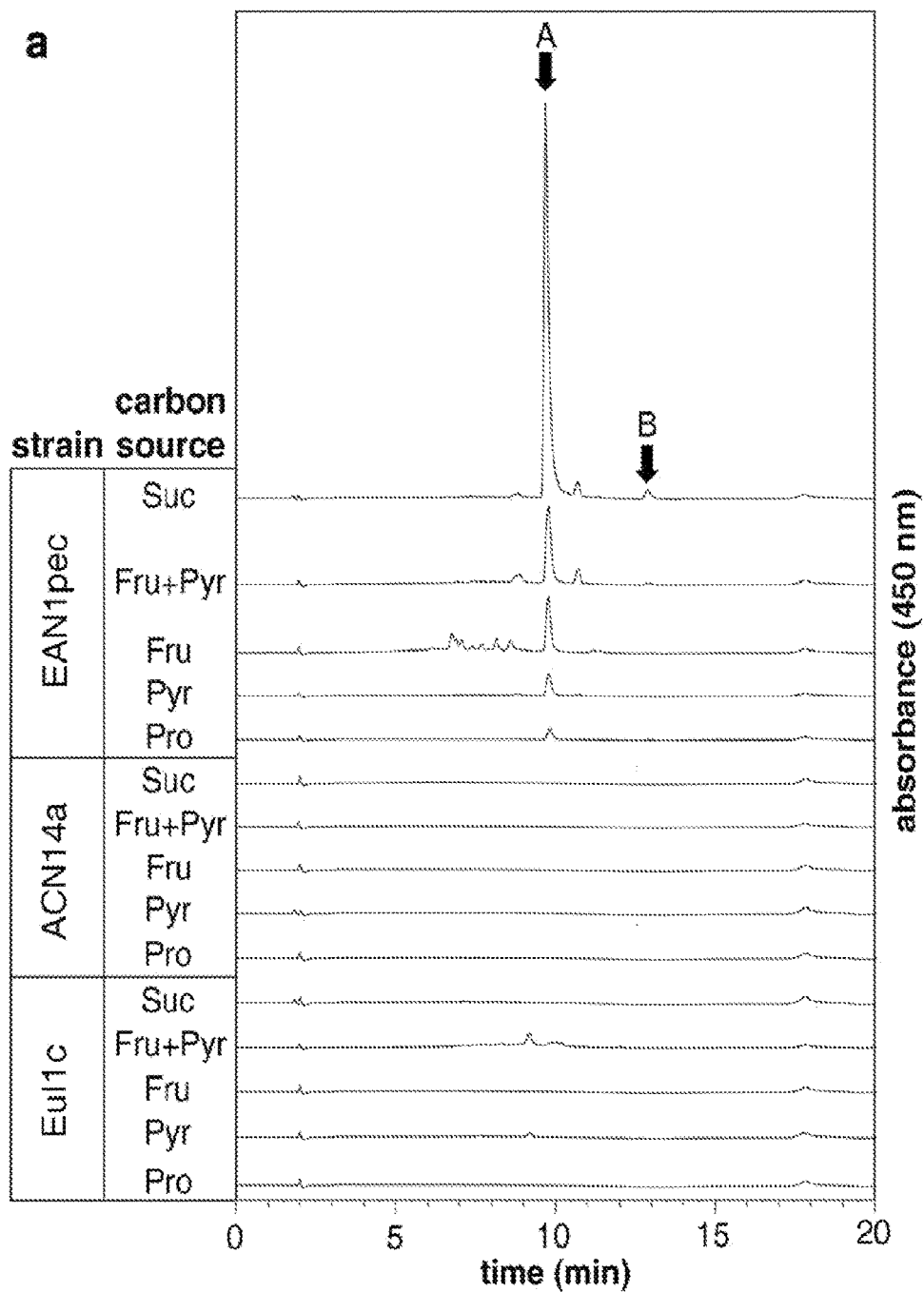
FIG. 6. UV-visible and mass spectral analysis of Frankia extracts and metabolites. a) HPLC analysis of extracts from the three Frankia species grown using different carbon sources, and showing the presence of the major compound (labeled A) and the minor compound (labeled B). b-g) ESI-MS analysis in positive and negative ionization modes and photodiode array (PDA) spectra of the major and minor peaks (data collected from 9.4-9.7 min, 12.7-12.9 min, respectively). b) major peak, positive mode (M+H–$H_2O$ and M+H–$2H_2O$); c) minor peak, positive mode (M+H, M+H–$H_2O$); d) major peak, negative mode (M–H, M–H–$CO_2$); e) minor peak, negative mode (M–H, M–H–$CO_2$); f) PDA spectrum of the major peak; g) PDA spectrum of the minor peak.
Figure 6:
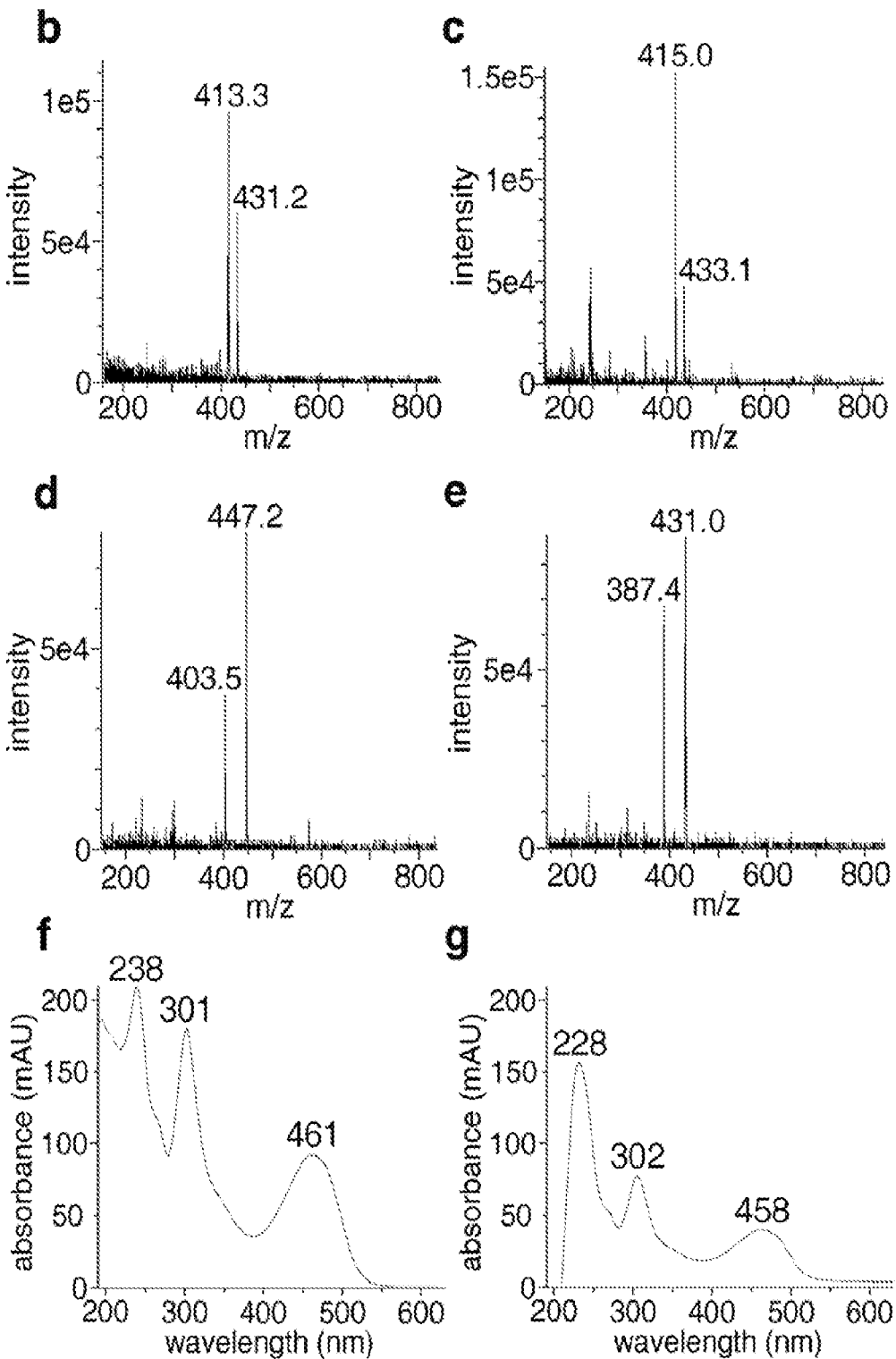

Because media composition can impact natural product production, each of the three remaining strains (*Frankia alni* ACN14a, *Frankia* sp. EAN1pec, and *Frankia* sp. EuI1c) was cultured in small scale (50 mL) in five different media that differed with respect to the carbon source(s): fructose, pyruvate, fructose+pyruvate, succinate, or propionate. Extracts from each of these fifteen strain/media combinations were obtained by adsorption onto and elution from Amberlite XAD-7 resin, and were analyzed by HPLC-PDA/MS. While extracts from *Frankia alni* ACN14a and *Frankia* sp. EuI1c showed no major UV-visible or mass spectral peaks in any of the five media, the extracts obtained from *Frankia* sp. EAN1pec showed one major peak [r.t.=9.7 min, ESI-positive m/z=413.3 (M+H−2H$_2$O), 431.2 (M+H−H$_2$O); ESI-negative m/z=403.5 (M−H−CO$_2$), 447.2 (M−H)] and one minor peak [r.t.=12.9 min, ESI-positive m/z=415.0 (M+H−H$_2$O), 433.1 (M+H); ESI-negative m/z=387.4 (M−H−CO$_2$), 431.0 (M−H)], each with absorption in the visible range (FIG. 6*a-e*). The UV-visible spectra of the major and minor compounds closely resembled each other, displaying peaks at ~300 and ~460 nm (FIG. 6*f-g*), suggesting that they are congeners. Production of these two compounds was highest with succinate as the sole carbon source, reached significant levels with either fructose alone or with fructose and pyruvate, and was low with either pyruvate or propionate alone (FIG. 6*a*). Extracts containing large amounts of these compounds displayed a deep red color not present in *Frankia alni* ACN14a or *Frankia* sp. EuI1c extracts. The lack of detectable products in *Frankia alni* ACN14a and *Frankia* sp. EuI1c may be due to their natural product biosynthetic gene clusters being cryptic—transcriptionally inactive—under the culture conditions used. The high resolution ESI-TOF MS of the major compound, frankiamicin A (m/z: [M−H] calculated for C$_{24}$H$_{15}$O$_9$ 447.0716; found 447.0709), supported the notion that the KSα/β from the clusters in question produces a 24-carbon aromatic polyketide. The minor compound, frankiamicin B, has an apparent mass of 432.

Isolation and Structure Elucidation of Frankiamicin A

Figure 11:
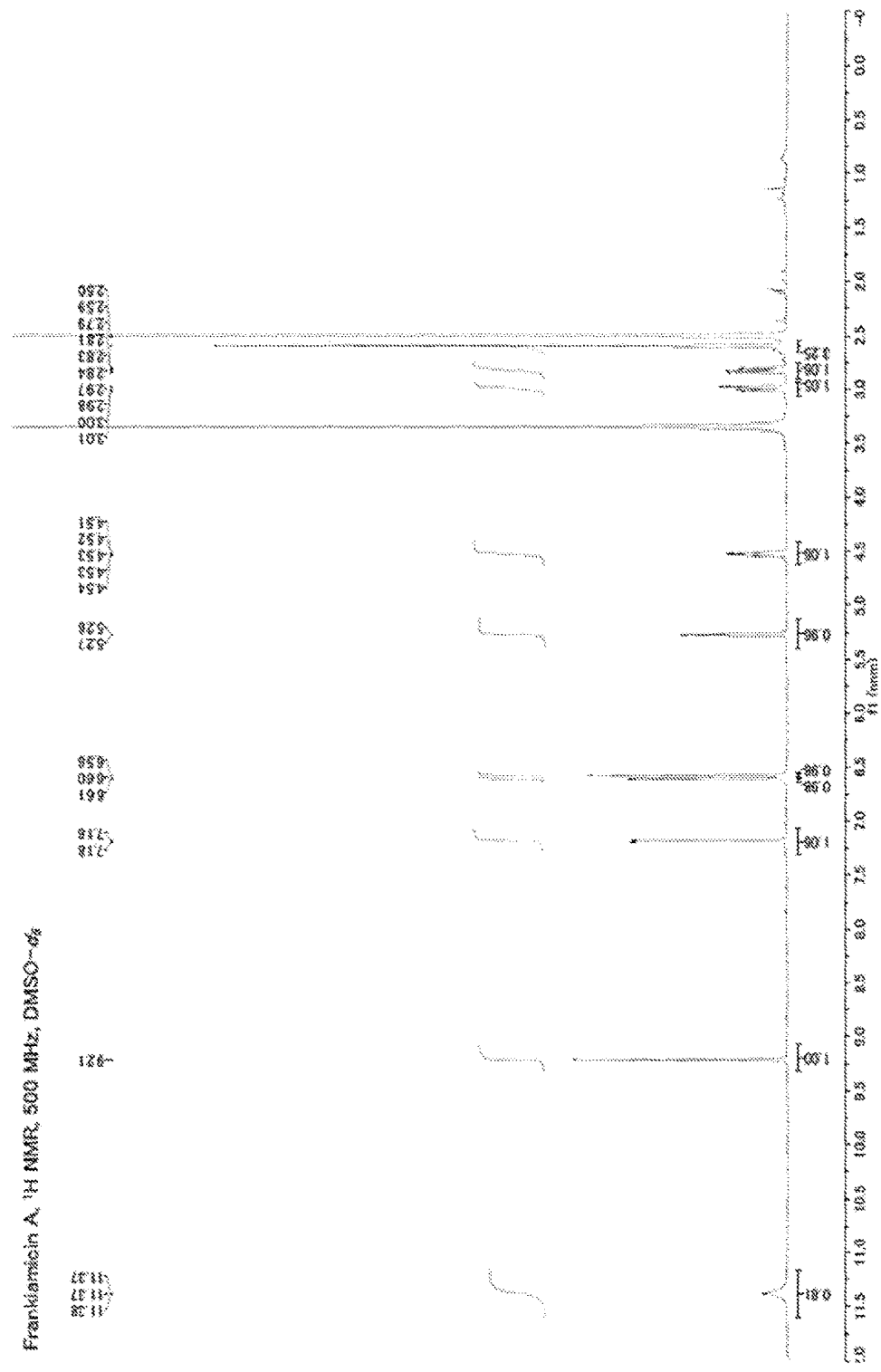
FIG. 11. $^1$H NMR spectrum of frankiamicin A (4).
Figure 12:
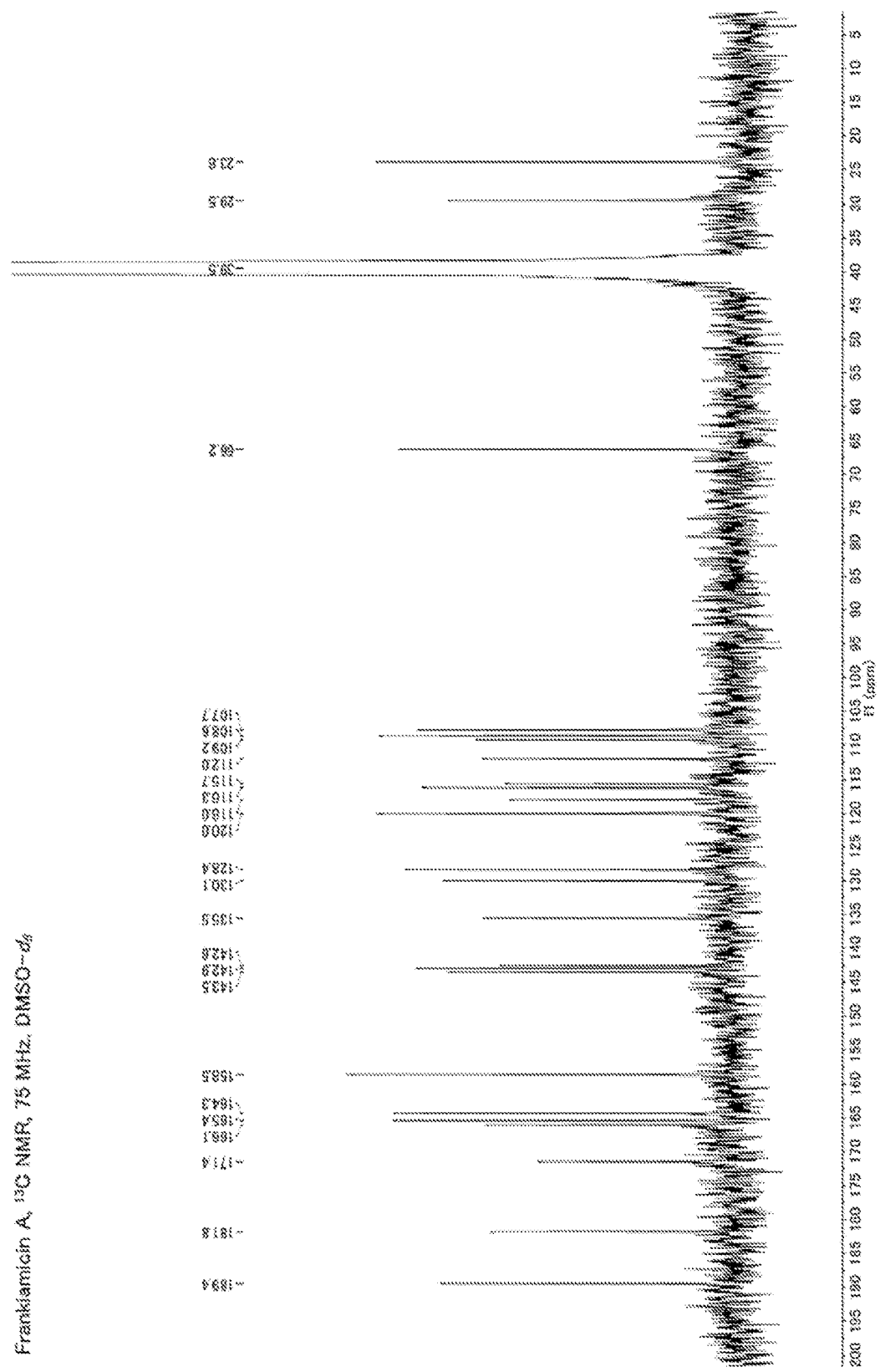
FIG. 12. $^{13}$C NMR spectrum of frankiamicin A (4).
Figure 13:
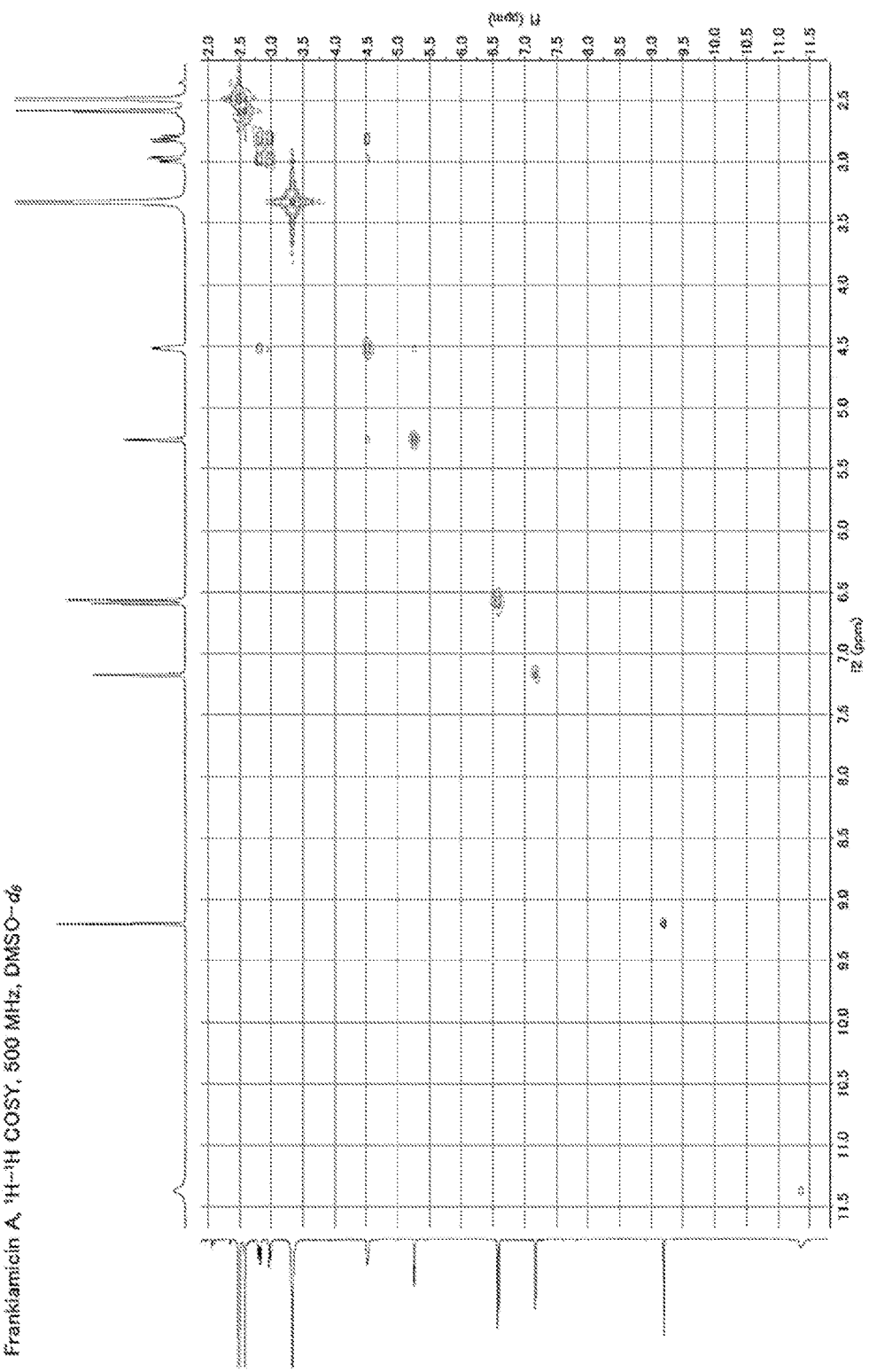
FIG. 13. $^1$H-$^1$H COSY spectrum of frankiamicin A (4).

Cultures of *Frankia* sp. EAN1pec were scaled up in a stepwise fashion to 3.6 L total volume from an initial seed culture over a six-month period, and 3.6 mg of frankiamicin A was isolated from the resulting culture broth by a three step chromatographic procedure. Frankiamicin A is an orange amorphous solid that is soluble in water and DMSO. $^1$H and $^{13}$C NMR spectral data (TABLE 1, FIG. 11, FIG. 12) reveal the presence of 10 proton and 24 carbon signals, consistent with high resolution MS analysis. Nineteen of the 24 carbon signals present in the $^{13}$C NMR spectrum have chemical shifts between δ 100 and 170 ppm, consistent with aromatic carbon atoms; and two carbonyl resonances were observed at 189.5 and 181.8 ppm, consistent with frankiamicin A being an aromatic polyketide compound with a quinone moiety. The $^1$H NMR spectrum of frankiamicin A displays four aromatic proton signals, one aliphatic proton signal with an adjacent hydroxyl group, one pair of geminal protons (2.98 and 2.81 ppm, J=15.6 Hz), one aromatic methyl group (2.58 ppm), and two exchangeable protons (11.37 and 5.26 ppm). $^1$H-$^1$H COSY (FIG. 13) NMR coupling constants demonstrate connectivity between H-5 (4.52 ppm) and both protons at C-6 (2.98, 2.81 ppm) and between H-5 and the exchangeable proton at 5.26 ppm. Two aromatic protons (H-10, H-12; 6.60 and 7.17 ppm, respectively) are coupled to each other with coupling constant of 2.1 Hz, suggesting a meta relationship. The $^1$H NMR signals of the remaining two aromatic protons and the methyl group were singlets.

TABLE 1

NMR spectroscopic data (DMSO-d$_6$) for frankiamicin A (4)

| position | δ$_H$ (multiplicity, J in Hz) | δ$_C$ | J $^{13}$C-$^{13}$C[a] |
|---|---|---|---|
| 1 |  | 164.3 [b] | [b] |
| 2 |  | 118.0 | 62.3 |
| 3 |  | 143.5 | 45.6 |
| 4 | 6.58 (s) | 116.3 | 59.8 |
| 4a |  | 143.0 | 60.6 |
| 5 | 4.53 (dt, 8.9, 4.6) | 66.3 | 37.6 |
| 6 | 2.83 (dd, 15.8, 8.9) 2.98 (dd, 15.8, 4.6) | 29.5 | 37.7 |
| 6a |  | 128.4 | 69.3 |

TABLE 1-continued

NMR spectroscopic data (DMSO-d₆) for frankiamicin A (4)

| position | $\delta_H$ (multiplicity, J in Hz) | $\delta_C$ | J $^{13}$C-$^{13}$C[a] |
|---|---|---|---|
| 7 | | 158.5 | 69.1 |
| 7a | | 112.0 | 56.9 |
| 8 | | 189.4 | 56.0 |
| 8a | | 109.2 | 64.9 |
| 9 | | 165.4 [b] | [b] |
| 10 | 6.60 (d, 2.1) | 107.7 | 66.8 |
| 11 | | 166.1 [b] | [b] |
| 12 | 7.18 (d, 2.1) | 108.6 | 64.1 |
| 12a | | 135.5 | 64.5 |
| 13 | | 181.8 | 55.1 |
| 13a | | 130.1 | 55.5 |
| 14 | 9.20 (s) | 120.0 | 56.2 |
| 14a | | 142.6 | 56.5 |
| 14b | | 115.7 | 63.9 |
| 15 | 2.58 (s) | 23.8 | 43.0 |
| 16 | | 171.4 | 64.4 |
| 5-OH | 5.27 (d, 4.6) | | |

Figure 7:
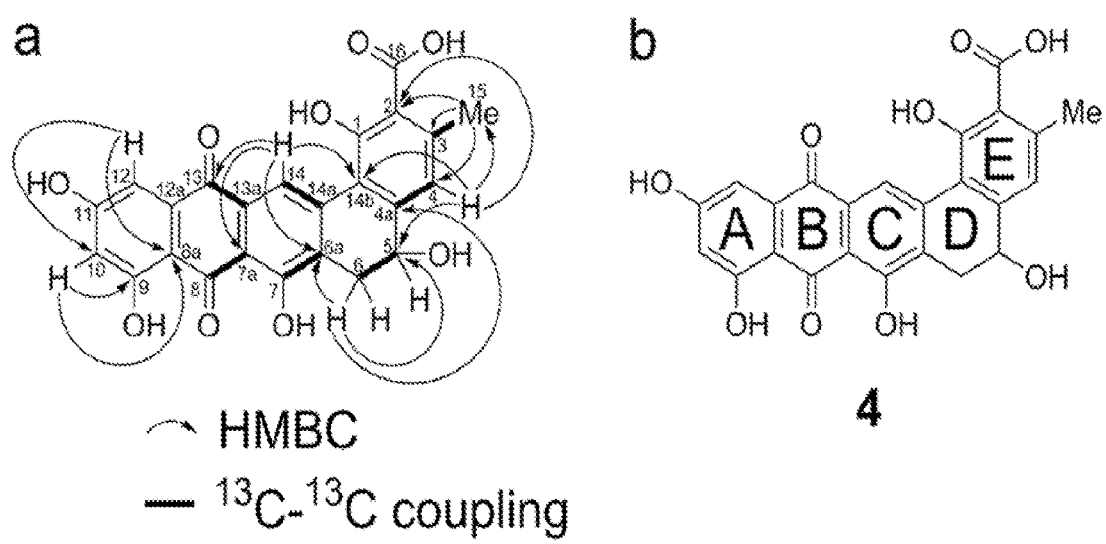
FIG. 7. Structural analysis and elucidation of frankiamicin A (4). a) HMBC correlations and $^{13}C$-$^{13}C$ couplings observed through [1,2-$^{13}C_2$]acetate feeding. b) structure of frankiamicin A.
Figure 14:
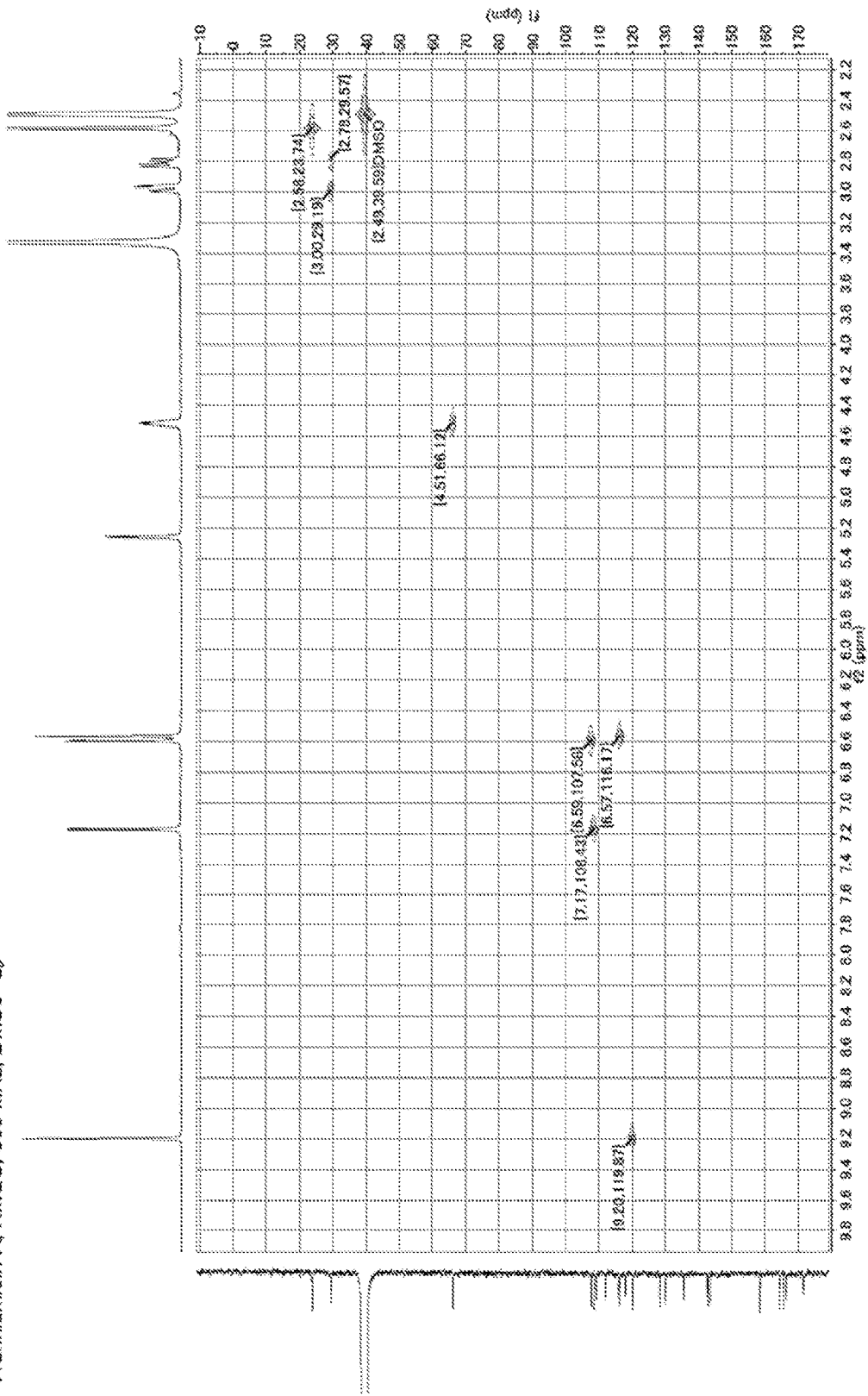
FIG. 14. HMQC spectrum of frankiamicin A (4).
Figure 15:
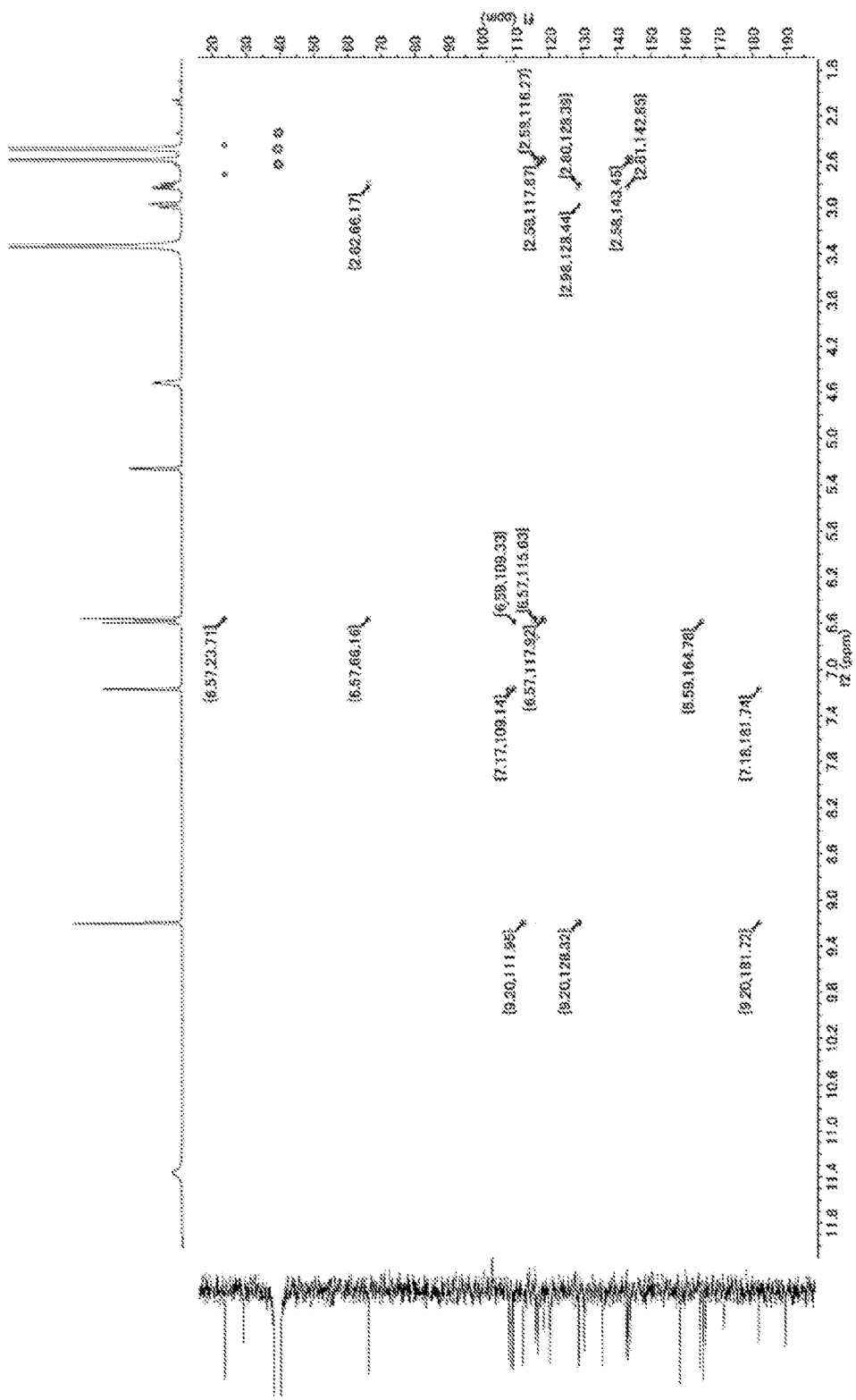
FIG. 15. HMBC spectrum of frankiamicin A (4).

[a]Coupling constants in Hz, observed by [1,2-$^{13}$C₂]acetate feeding
[b]Obscured by overlapping Single and multiple bond C—H correlations were elucidated by HMQC and HMBC experiments, respectively. The HMQC spectrum (FIG. 14) was used to assign the signals of the seven carbon atoms that are directly connected to protons. $^{13}$C chemical shifts indicate that three of these (C-15, C-5, and C-6) are sp$^3$ hybridized, and four (C-4, C-10, C-12, and C-14) are sp$^2$ hybridized. The HMBC spectrum (FIG. 7a, FIG. 15) showed that one of the carbonyl carbons (C-13, 181.8 ppm) has long range connectivity to two aromatic protons (H-12 and H-14). HMBC correlations from H-14 and H-6 to C-6a, and from H-14 and H-4 to C-14b were also observed, suggesting the structure of rings A-D of frankiamicin A. Further HMBC correlations from H-15 to C-2, C-3, and C-4; and from H-4 to C-2 and C-15 placed the methyl group at C-3, and allowed us to propose the structure of frankiamicin A as 4 (FIG. 7b).

Since C—H correlations for eight carbon atoms (C-1, C-7, C-8, C-11, C-12a, C-13a, C-14a, and C-16) could not be observed through either HMQC or HMBC analyses, a $^{13}$C enrichment study using [1,2-$^{13}$C₂]acetate was carried out to obtain additional information on carbon atom connectivity. Frankia sp. EAN1pec cells obtained from a 0.5 L initial culture were grown in 1 L of fresh media for 17 days while supplementing with 250 mg of sodium [1,2-$^{13}$C₂] acetate on days 2, 5, 8, and 11 to obtain frankiamicin A that was partially labeled with intact [1,2-$^{13}$C₂]acetate units. The resulting compound (1.3 mg) was purified and analyzed by $^{13}$C NMR spectroscopy (FIG. 16). In the spectrum obtained, all carbon signals are doublets that correspond to singlet signals in the $^{13}$C spectrum of the unlabeled compound. The $^{13}$C-$^{13}$C spin couplings observed originate from intact incorporation of [1,2-$^{13}$C₂]acetate units into frankiamicin A, while $^{13}$C-$^{13}$C spin couplings between two different acetate units are not observed due to the low incorporation ratio of labeled acetate. Analysis of coupling constants (FIG. 7a, TABLE 1, right column) clearly elucidated connectivity of C3 and C15, C4 and C4a, C5 and C6, C6a and C7, C7a and C8, C13 and C13a, and C14 and C14a. The four signals corresponding to C-14b, C-1, C-2, and C-16 are all doublets with similar coupling constants, indicating that these four carbon atoms are collectively derived from incorporation of two intact acetate units. Similarly, the remaining six carbon atoms, C-8a, C-9, C-10, C-11, C-12, and C-12a, whose coupling constants are also similar, are collectively derived from incorporation of three intact acetate units. The results of 1-D and 2-D NMR studies of the unlabeled compound together with analysis of the $^{13}$C spectrum of the labeled compound provide strong support for the proposed structure of frankiamicin A as the 24-carbon pentangular polyketide 4.

The structure of 4 together with the fact that Frankia sp. EAN1pec harbors only a single type II polyketide cluster strongly support the idea that 4 is produced by this cluster. The highly conserved gene composition and arrangement, and the high degree of sequence similarity observed among the group of Frankia type II polyketide gene clusters analyzed suggests that each of them is responsible for production of 4 or a closely-related, minimally-tailored 24-carbon pentangular polyketide. Thus, the Frankia KSα/β enzymes represent a new group of 24-carbon poly-β-ketone synthesizing KSα/β that has diverged in sequence from homologues that produce the same intermediate. Furthermore, the structure of 4 strongly supports the idea that the immediate tailoring enzymes in the Frankia clusters collectively function to produce a pentangular, rather than a tetracenomycin, or atypical polyketide core structure. Interestingly, an engineered compound JX134, which is identical in structure to 4, was produced by heterologous expression of a set of nine pradimicin biosynthetic genes, including eight that are homologues of genes in the Frankia clusters, supporting the idea that homologous genes in the two clusters are functionally equivalent.

The minor congener observed during initial LC-MS analysis, frankiamicin B, was present in sufficiently small quantities (1% of frankiamicin A) to preclude NMR structural analysis, but is likely G-2A (5, FIG. 8), the 5-deoxy derivative of frankiamicin A that was previously isolated, together with its C-2 decarboxylated congener G-2N, from Frankia sp. G2. This, together with our comparative genomic analysis of the Frankia clusters, suggests that the ability to produce G-2A and congeners is well-conserved among Frankia species, and that G-2A and G-2N are produced in Frankia sp. G2 by a gene cluster analogous to those identified in sequenced Frankia genomes.

Biosynthesis of Frankiamicin A

Each gene in the Frankia sp. EAN1pec cluster was assigned a systemic name. These names, their corresponding locus tags, GI numbers, and proposed functions are summarized in TABLE 2. TABLE 7 is an expansion of TABLE 2, containing comparative genomic information on all homologous gene clusters from five Frankia species and on all pentangular and tetracenomycin training set clusters.

TABLE 2

Frankiamicin (fkm) cluster genes, homologues, and proposed functions

| Gene | Locus Tag | GI# | Homologues | | | Annotation | Proposed Function |
| | | | tcm | pdm | ben | | |
|---|---|---|---|---|---|---|---|
| fkmR1 | FranEAN1_2384 | 158314214 | — | — | — | signal transduction histidine kinase | Cluster regulation by signal transduction |

TABLE 2-continued

Frankiamicin (fkm) cluster genes, homologues, and proposed functions

| Gene | Locus Tag | GI# | Homologues tcm | Homologues pdm | Homologues ben | Annotation | Proposed Function |
|---|---|---|---|---|---|---|---|
| fkmR2 | FranEAN1_2385 | 158314215 | — | — | — | Roadblock/LC7 family protein | Cluster regulation by signal transduction |
| fkmR3 | FranEAN1_2386 | 125314216 | — | — | — | protein of unknown function DUF742 | Cluster regulation by signal transduction |
| fkmR4 | FranEAN1_2387 | 125314217 | — | — | — | GTPase | Cluster regulation by signal transduction |
| fkmR5 | FranEAN1_2388 | 125314218 | — | — | — | LuxR family transcriptional regulator | cluster regulation |
| fkmC3 | FranEAN1_2389 | 125314219 | tcmI | pdmK | benE | polyketide synthesis cyclase | D, E ring cyclization |
| fkmC | FranEAN1_2390 | 125314220 | tcmM | pdmC | benC | acyl carrier protein | acyl carrier protein |
| fkmC1 | FranEAN1_2391 | 125314221 | tcmN | pdmD | benH | cyclase/dehydrase | A, B ring cyclization |
| fkmC2 | FranEAN1_2391 | 125314222 | tcmJ | pdmL | benD | cupin fold family | C ring cyclization |
| fkmA | FranEAN1_2393 | 125314223 | tcmK | pdmA | benA | B-ketoacyl synthase | ketosynthase α |
| fkmB | FranEAN1_2394 | 125314224 | tcmL | pdmB | benB | β-ketoacyl synthase | ketosynthase β |
| fkmD | FranEAN1_2395 | 125314225 | — | pdmG | benL | ketoreductase | C-6 reduction |
| fkmO1 | FranEAN1_2396 | 125314226 | — | pdmH | benH | putative ABM monooxygenase | quinone formation/D, E ring cyclization |
| fkmO2 | FranEAN1_2397 | 125314227 | — | pdmI | benJ | Putative ABM monooxygenase | quinone formation/D, E ring cyclization |

Figure 8:
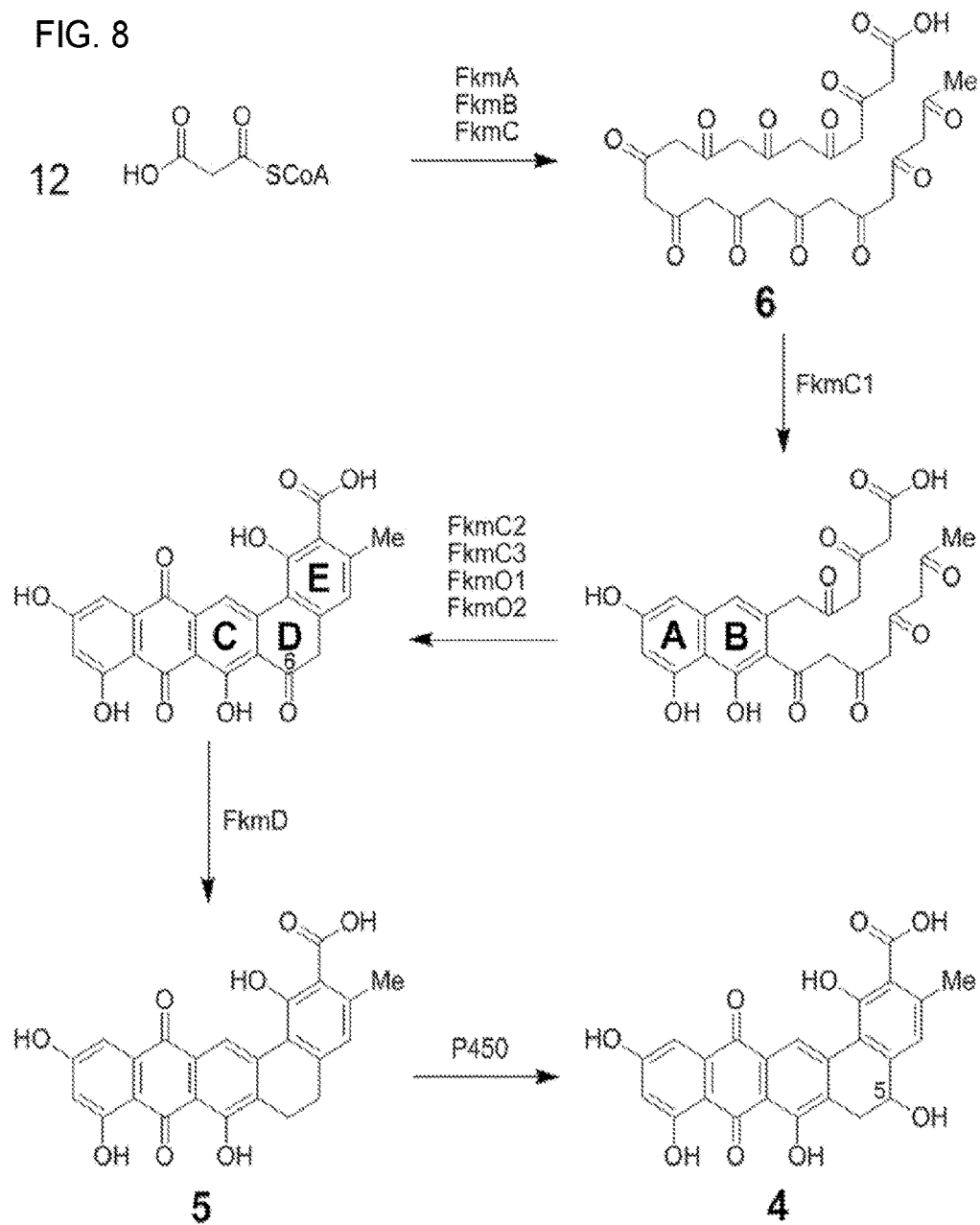
FIG. 8. Proposed frankiamicin A biosynthetic pathway. The minimal polyketide synthase FkmABC catalyze conversion of 12 malonyl-CoA units to the 24 carbon poly-β-ketone 6; TcmN-like aromatase/cyclase FkmC1 catalyzes closure and aromatization of rings A and B; FkmC2, C3, O1, and O2 catalyze closure of the C, D, and E rings, aromatization of the C and E rings, and oxygenation of the B ring; FkmD catalyzes reduction of the C-6 ketone to form G-2A (5); and a P450 monooxygenase catalyzes C-5 hydroxylation to generate frankiamicin A (4).

In light of the structure of 4 and the gene composition of the *Frankia* type II polyketide clusters analyzed here, the biosynthesis of the frankiamicin polyketide core structure appears to follow closely that proposed for pradimicin, which shares the same core structure. The FkmA, FkmB, and FkmC proteins correspond to the KSα, KSβ, and ACP minimal polyketide synthase genes, respectively. These three proteins may act in concert to produce the 24-carbon poly-β-ketone intermediate 6 via 11 cycles of Claisen condensation (FIG. 8).

The three cyclases found in the cluster, FkmC1, FkmC2, and FkmC3, are homologous to TcmN/PdmD, TcmJ/PdmL, and TcmI/PdmK, respectively, from tetracenomycin and pradimicin pathways. Homologues of these three cyclases are invariably present in type II polyketide gene clusters belonging to the pentangular and tetracenomycin subclasses. Precise assignment of the substrates and products of cyclases and other immediate tailoring enzymes is notoriously difficult due to the high reactivity of the poly-β-ketone-containing cyclization intermediates. Also, these enzymes form complexes with the minimal polyketide synthase in which they act interdependently, and serve both catalytic and structural roles. Cyclase functions are usually inferred from in vitro and in vivo analysis of shunt metabolites accumulated when the minimal polyketide synthase and specific sets of cyclases are present. Through such studies, homologues of FkmC1, TcmN, and PdmD, have been shown to cyclize and aromatize both the A and B rings of the nascent aromatic polyketide. Predicted cupin-like fold cyclases TcmJ and PdmL, homologues of FkmC2; and predicted ferredoxin-like fold cyclases TcmI and PdmK, homologues of FkmC3, were each shown to be essential for efficient production of the fully cyclized aromatic polyketide cores in their respective pathways. TcmI was shown in vitro to catalyze closure of the tetracenomycin D ring. Thus, FkmC2 and its homologues may be involved in efficient closure and aromatization of the C ring. Also, FkmC3 and its homologues may be involved in efficient closure of the D ring, and possibly in cyclization and aromatization of the E ring in pentangular pathways (FIG. 8, TABLE 2).

FkmO1 and FkmO2, two antibiotic biosynthesis monooxygenase (ABM) superfamily members, are also present in the cluster. Homologues of both are present in, and encoded by adjacent co-directional genes in all training set pentangular clusters. The closest characterized homologues of FkmO1 and FkmO2 are PdmH and PdmI, respectively, from the pradimicin pathway. Heterologous expression studies demonstrated that PdmH is required for formation of rings C through E of the pentangular core structure whereas PdmI was shown to be non-essential. More distantly related ABM superfamily members from type II polyketide pathways whose reactions have been characterized in vitro, such as TcmH, ActVA-ORF6, AknX, and SnoaB catalyze oxygenation of the anthrone B ring to generate a quinone. This led to the suggestion that PdmH catalyzes an analogous reaction in pradimicin biosynthesis. However, all B ring oxygenation reactions characterized in vitro thus far occur as tailoring steps after the aromatic core structure is formed, whereas PdmH is proposed to act in concert with cyclases PdmL and PdmK at some point amid cyclization of rings C through E. Cyclase TcmI and anthrone oxygenase ActVA-ORF6 have strong topological similarity and share the ferredoxin-like fold. This suggests an evolutionary, and possibly a functional link, between TcmI-like cyclases and ABM superfamily members. It is therefore possible that ABM superfamily members FkmO1 and FkmO2 and their homologues may be involved in pentangular polyketide cyclization. In light of (a) the conservation of homologues of both proteins in the eleven pentangular clusters sequenced thus far but not in tetracenomycin class clusters and (b) the conserved adjacent co-directional arrangement of their encoding genes, both FkmO1 and FkmO2 and their homologues may be immediate tailoring enzymes that may be involved in B ring oxygenation and/or E ring cyclization and aromatization (FIG. 8, TABLE 2).

The gene product of FkmD is homologous to ketoreductases from pentangular pathways such as BenL and PdmG from benastatin and pradimicin pathways, respectively. Homologues of FkmD are invariably present in pentangular clusters. Both BenL and PdmG can catalyze reduction of the ketone at C-6 of the pentangular core structure. This occurs as a tailoring step after polyketide cyclization and B ring quinone formation. In studies of pradimicin biosynthesis, expression of PdmG along with the minimal polyketide synthase, cyclases, and monooxygenase led to a fully reduced C5-C6 bond, demonstrating that C-6 dehydration and a second reduction at C-6 occur. Most pentangular polyketides whose biosynthesis has been studied thus far have a fully reduced C5-C6 bond. FkmD may catalyze C-6 ketoreduction, C5 dehydration and aromatization, and C-6 enoylreduction to generate G-2A (5) (FIG. 8). LanV, a ketoreductase from the landomycin pathway, a type II polyketide of the angucycline subclass and homologue of FkmD, catalyzes both C-6 ketoreduction and C5 dehydration/aromatization of the angucycline core structure in an analogous manner.

The final step in the proposed biosynthesis of frankiamicin A (4) is C-5 hydroxylation. A cytochrome P450 monooxygenase PdmJ was shown to introduce a hydroxyl group at the C-5 position in the biosynthesis of pradimicin. This modification is not conserved in pentangular pathways, but also likely occurs in FD-594 biosynthesis based on the presence of a C-5 hydroxyl in the structure and a close homologue of PdmJ in the cluster. Surprisingly, a likely candidate for C-5 hydroxylation of G-2A to generate frankiamicin A is absent from both the *Frankia* sp. EAN1pec cluster and its homologues in other *Frankia* genomes. While it is unclear from bioinformatic analysis which enzyme might be responsible for C-5 hydroxylation in *Frankia* sp. EAN1pec, or whether this modification is conserved in the *Frankia* type II polyketide pathways analyzed, several P450 enzyme candidates, including nearby Franean1_2408, are encoded in the *Frankia* sp. EAN1pec genome.

Signal Transduction and Regulatory Proteins in the Fkm Cluster

The frankiamicin gene cluster encodes several proteins (FkmR1-FkmR5) with homology to proteins involved in transcriptional regulation and signal transduction. Among these, FkmR5 is homologous to members of the LuxR family of transcriptional regulators, which are commonly found at the edges of natural product biosynthetic gene clusters and have been found to function as cluster-specific regulators (CSRs) that can either activate or repress transcription of natural product gene clusters. The four gene cassette fkmR1-fkmR4 is homologous to a conserved set of genes termed the conservon that are present in a number of Actinobacterial genomes. The existence of the conservon was first noted after sequencing the *Streptomyces coelicolor* A3(2) genome, which harbors 13 copies of this gene cassette. Subsequent genetic and biochemical studies of one *S. coelicolor* conservon, cvn9, showed that these proteins form a membrane associated complex that includes an integral membrane histidine kinase, Ras-like GTPase, and two accessory proteins. The Cvn9 complex was shown to be involved in regulation of morphological differentiation and antibiotic production. Conservon homologues can act as signal transducers that receive environmental signals and stimulate intracellular responses. The presence of the fkmR1-R4 conservon within the fkm operon suggests that it transduces an extracellular signal into an intracellular response that leads to activation or repression of frankiamicin cluster expression, possibly via interaction with FkmR5. Homologues of fkmR1-R4 are not known to occur as part of any natural product biosynthetic gene clusters studied to date, suggesting that the fkm cluster may be regulated differently than other natural product clusters.

Bioactivity Assays of Frankiamicin A

Unlike the vast majority of other type II polyketide natural products studied to date, which were identified through bioactivity-guided approaches, frankiamicin A was discovered through a bioinformatics-guided approach. Therefore, nothing was known a priori about its bioactivity. Compared to frankiamicin A, many other members of the pentangular type II polyketide subclass with diverse bioactivities such as pradimicin, fredericamycins, lysolipin, and A-74528 undergo extensive tailoring modifications that substantially alter the polyketide core structure. Several bioactive compounds that have less substantial structural modifications to the polyketide core, and are therefore more similar to frankiamicin A, are known. These include the antibacterial BE-39589 group, the phosphodiesterase inhibitor KS-619-1, and the glutathione S-transferase inhibiting benastatins and bequinostatins.

The bioactivity of frankiamicin A was assayed against several bacterial, fungal, and protozoal strains; and cancer cell lines (TABLE 3). Frankiamicin A exhibited detectable antimicrobial activity against both wild-type and methicillin-resistant *S. aureus* (MRSA).

As used herein, the term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Materials and Methods
General

All chemicals including media components were purchased from Sigma-Aldrich (St. Louis, Mo.), VWR (Radnor, Pa.) or Fisher Scientific (Pittsburgh, Pa.) and were used without further purification. HPLC analysis was performed using a Dionex Ultimate 3000 instrument equipped with a photo diode array (PDA) detector and the specified column (see below). LC-MS analysis was performed using an API 2000 electrospray ionization (ESI) mass spectrometer (AB SCIEX) connected to the HPLC system. Post-column splitting (1:4) was used to simultaneously monitor MS and UV-visible spectra. NMR spectra were obtained using Bruker Avance III 300 and Avance 500 spectrometers housed in the NMR Core Facility in the Department of Chemistry and Chemical Biology at the University of New Mexico. Chemical shifts (δ in parts per million) are reported relative to that of the solvent peak (δ=2.50 ppm and 39.5 ppm for DMSO-$d_6$ in $^1H$ and $^{13}C$ NMR spectra, respectively). High resolution MS data was obtained using a Waters LCT Premier ESI-TOF mass spectrometer housed in the Mass Spectrometry and Proteomics Core Facility in the Department of Chemistry and Chemical Biology at the University of New Mexico. Vector NTI Advance 10 (Life Technologies, Carlsbad, Calif.) was used for routine sequence analysis.

Bioinformatic Analysis

Figure 9:
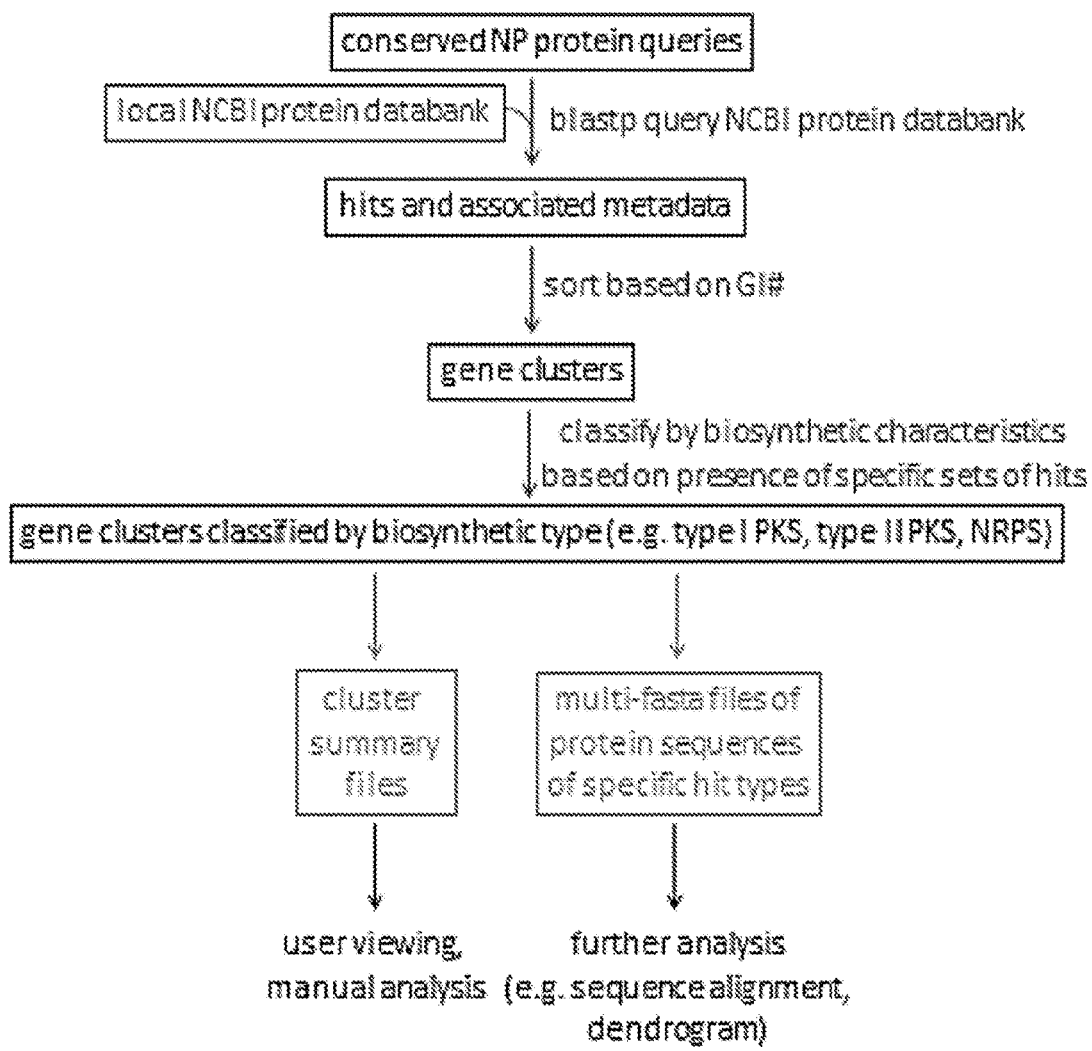
FIG. 9. Schematic summary of DYNAMITE (Ogasawara et al., 2015, PLoS ONE 10(4): e0121505) workflow used in this study.

The Python-based software package DYNAMITE (Ogasawara et al., 2015, PLoS ONE 10(4): e0121505) was used to identify natural product biosynthetic gene clusters encoded in nucleotide/protein sequences within in the entire NCBI databank. The DYNAMITE automated workflow is as follows (see FIG. 9): 163 protein sequences representing many conserved protein families found in type I and type II polyketide and non-ribosomal peptide gene clusters are used to query a locally-housed NCBI protein databank using the blastp algorithm (Altschul et al. 1990, *J Mol Biol* 215:403-410). Hits and associated metadata (including species, GI number, and other attributes) obtained using these queries are sorted based on GI number, which arranges them according to their positions within genomes, identifying putative natural product gene clusters. Gene clusters are then classified by biosynthetic characteristics (type I polyketide synthase, type II polyketide synthase, non-ribosomal peptide synthetase) based on the presence of specific sets of hits within a particular GI number range. Summaries of the attributes (species, GI number range, arrangement of hit types from each gene cluster on the genome, biosynthetic classification) of all gene clusters found, as well as of gene clusters that conform to specific biosynthetic classifications, are output as text files that can be viewed and analyzed by the user. All protein sequences corresponding to specific hit types (e.g., KSα, K5β) from specific gene cluster biosynthetic types can also be compiled in a semi-automated manner using a script within DYNAMITE, and output as multi-fasta files for further analysis. Gene clusters displaying biosynthetic characteristics of interest can also be manually downloaded as .gb files from NCBI, guided by DYNAMITE summary files, and subjected to further manual analysis using standard software such as Vector NTI.

The ketosynthase α/β dendrogram was generated as follows: The amino acid sequences of all ketosynthase α and ketosynthase β enzymes identified by DYNAMITE were compiled as two separate multi-fasta files using a custom script. Each set was then aligned using Clustal Omega (Sievers et al., 2011, *Mol Syst Biol* 7:539) and unconserved N-terminal and C-terminal regions were trimmed based on the multiple sequence alignments to minimize their effects on tree building after constructing the concatenated sequence. Residues corresponding to positions 6-420 of the 424 amino acid actinorhodin KSα, and to positions 1-403 of the 407 amino acid actinorhodin KSβ were retained. Trimmed ketosynthase α/β sequence pairs were concatenated and aligned again using Clustal Omega. A bootstrapped maximum likelihood dendrogram was generated from the alignment using FastTree 2 (Price et al., 2010, PLoS ONE 5:e9490). The dendrogram was visualized and color coded using the Interactive Tree of Life (iTOL; Letunic I, Bork P., 2011, *Nucleic Acids Res* 39:W475-478) web interface. Ketosynthase I (FabB) from the *Escherichia coli* fatty acid biosynthetic pathway was treated similarly and used to construct a pseudo-dimer sequence that was used as the outgroup. The identities of the 64 studied type II polyketide systems and their starter and extender unit specificities were compiled manually by cross referencing DYNAMITE results with literature, and were color coded by type in iTOL. A high resolution version of the dendrogram in FIG. 3, including bootstrap values, species names, and training set compound names, is available in FIG. 10.

Cultivation of Bacterial Strains

*Frankia alni* ACN14a, *Frankia* sp. EAN1pec, and *Frankia* sp. EuI1c were maintained in *Frankia* Defined Minimal Medium (FDM) supplemented with the appropriate carbon source(s). *Frankia* sp. CcI3 and *Frankia* sp. EUN1f were maintained in CB Liquid Medium. Both FDM and CB media contain the following: 0.05% w/v $NH_4Cl$, 0.02% w/v $MgSO_4.7H_2O$, 0.1% v/v 1000× iron stock solution (0.75% w/v disodium ethylenediaminetetraacetic acid dihydrate, 0.56% w/v $FeSO_4.7H_2O$, and 0.02% w/v $Na_2MoO_4.2H_2O$). Additionally, FDM medium contains 0.05% w/v Bacto proteose peptone No. 3, 0.01% w/v $CaCl_2.7H_2O$, and 10% v/v 10× phosphate buffer stock solution (0.5 M potassium phosphate buffer, pH 6.5); while CB medium contains 5 g/L sodium pyruvate, 0.16% Bacto proteose peptone No. 3, 0.06% w/v $CaCl_2.7H_2O$, and 10% v/v 10×MOPS-phosphate buffer stock solution (50 mM potassium phosphate, 50 mM MOPS, pH 6.5). The 10× phosphate and phosphate-MOPS buffer stock solutions were added to the media after autoclaving. Fructose (5 g/L) and sodium pyruvate (5 g/L) together were used as the carbon source for *Frankia* sp. EAN1pec and *Frankia alni* ACN14a, and glucose (5 g/L) was used for *Frankia* sp. EuI1c.

Chromatographic and Spectral Analysis of *Frankia* Extracts

*Frankia* sp. EAN1pec, *Frankia alni* ACN14a, and *Frankia* sp. EuI1c were each cultured in a rotary incubator in 50 mL FDM media, each supplemented separately with five different carbon sources, in 500 mL Erlenmeyer flasks at 28° C., 250 rpm, for two weeks. Carbon sources tested were fructose (5 g/L), sodium pyruvate (5 g/L), fructose (5 g/L) plus sodium pyruvate (5 g/L), sodium succinate (5 g/L), and sodium propionate (5 g/L). The cultures were centrifuged to remove cells. The resulting supernatant was incubated with 5 mL of Amberlite XAD-7 resin, which was washed with 200 mL water. Resin-bound metabolites were eluted with 6 mL of MeOH and the solvent was removed by rotary evaporation. Each sample was re-dissolved in 0.5 mL of 50% aqueous acetonitrile. Ten µL of sample was subjected to LC-MS analysis. Separation was performed by linear gradient elution (0 to 100% solvent B over 12 minutes) on a C-18 column (Thermo Scientific ODS Hypersil, 5 µm, 150×3 mm). Solvent A: 5% aqueous acetonitrile, 0.1% formic acid; solvent B: 95% aqueous acetonitrile, 0.1% formic acid.

Isolation of Frankiamicin A (4)

The *Frankia* sp. EAN1pec culture was scaled up by stepwise unshaken growth at room temperature in Erlenmeyer flasks with increasing volumes of FDM-fructose/pyruvate media over a period of six months. After two to four weeks of growth, cells were collected by centrifugation, homogenized, and transferred to two- to four-fold the original volume of fresh media for the next growth period. After the final growth period, 3.6 L of culture was centrifuged (6000×g, 15 min.) to remove the cells. The resulting supernatant was mixed with 100 mL of Amberlite XAD-7 and the resin was loaded onto a column. The column was washed with water (2 L) and then with 20% aqueous MeOH (1 L). Frankiamicin A and minor congeners were eluted with 50% aqueous MeOH (500 mL). Fractions with red color were collected and concentrated by rotary evaporation. The residue was re-dissolved in 1 mL of water and loaded onto a Sep-Pack C18 column (2 g adsorbent, Varian). The column was washed with 10 mL of water and the desired compounds eluted with 10 mL MeOH. After evaporation of the solvent, the extract was re-dissolved in 2 mL of 10% aqueous MeOH and further purified by HPLC. Purification was performed by linear gradient elution (5 to 95% solvent B over 12 min) on a semi-preparative C-18 column (Thermo Scientific ODS Hypersil, 5 µm, 150×10 mm) at a flow rate of 4 mL/min. Solvent A: water; solvent B: acetonitrile. Frankiamicin A has a retention time of eight minutes under these conditions, and was collected manually. Solvent was removed by rotary evaporation and was dried under high vacuum overnight, yielding 3.6 mg of an orange solid.

Supplementation with isotopically-labeled acetate was carried out as follows. Because of its extremely slow growth rate, *Frankia* sp. EAN1pec cells from a previous 0.5 L culture were inoculated into 1 L of fresh FDM-fructose/pyruvate medium and grown in a rotary incubator at 28° C., 250 rpm. An aqueous solution (4 mL) containing 1.0 g of sodium [1,2-$^{13}C_2$]acetate (99 atom % $^{13}C$, Aldrich) and 1.0 g of non-labeled sodium acetate was prepared and sterilized by filtration through a syringe filter (pore size: 0.2 µm). Pulse feeding was performed by adding 1 mL of the solution to the culture 2 days, 5 days, 8 days, and 11 days after inoculation. The total concentration of sodium [1,2-$^{13}C_2$] acetate added was 0.1% w/v. After 17 days, the culture was harvested by centrifugation at 6000 g for 15 minutes. The $^{13}C$-labeled frankiamicin A was isolated from the supernatant as described above. The purified compound was analyzed by $^{13}C$ NMR spectroscopy and the spectrum compared to that of unlabeled compound. The chemical shifts of individual $^{13}C$ signals differed slightly between labeled and unlabeled compounds, likely due to slight conformational differences. To resolve these differences, labeled compound was doped with unlabeled and again analyzed by $^{13}C$ NMR (FIG. 16).

Bioactivity Assays

Antimicrobial and anticancer assays were conducted by quantifying viability of cells exposed to frankiamicin A (2-fold serial diluted in DMSO) at concentrations ranging from 0-100 µM using an MTT assay (Frolova et al., 2013, *J Med Chem* 56:6886-6900). For antimicrobial assays, a liquid culture of each test strain was grown overnight at 37° C. in TSB media in a rotary incubator. The resulting culture was diluted 1:100 into fresh media and 100 µL aliquots were transferred to a 96-well plate. Serial diluted compound was added to individual wells and cells were incubated at 37° C. for either 6 hours or 18 hours prior to MTT assay. Anticancer assays were conducted using approximately 4000 cells incubated overnight at 37° C. in 100 µL DMEM media supplemented with 10% FBS, adding serial diluted compound, and incubating for 48 hours prior to MTT assay. Assays of *T. cruzi* (ATCC 30013) were conducted by growing cells unshaken at 25° C. in ATCC Medium 1029 (LIT Medium) for five days, diluting 1:10 into fresh media, adding 100 µM frankiamicin A, incubating for an additional eight days, and assessing cell viability by microscopy using an untreated control for comparison.

TABLE 3

Frankiamicin A bioactivity assay results

| Test strain/cell | IC$_{50}$ (µM) | MIC (µM)[a] | MIC (µM)[b] |
|---|---|---|---|
| He | >1 | — | — |
| MC | >1 | — | — |
| Jurk | >1 | — | — |
| C. albicans | >1 | — | — |
| T. | >1 | — | — |
| S. pyogenes | — | >1 | >1 |
| A. baumanii | — | >1 | >1 |
| P. aeruginosa | — | >1 | >1 |
| Y. pestis | — | >1 | >1 |
| S. aureus | — | ~1 | >1 |
| MRS | — | ~ | >1 |

[a]Assessed after 6 h incubation
[b]Assessed after 18 h incubation

TABLE 4

List of ketosynthase α/β genes used to construct the dendrogram shown in FIG. 3.

| PKS_Cluster_ID | Strain name | Compound name | starter unit - number of cycles | NCBI gi Ksα | NCBI gi KSβ gi |
|---|---|---|---|---|---|
| 179 | Saccharopolyspora hirsuta | | | 347180 | 347181 |
| 198 | Kibdelosporangium aridum | | | 406081 | 406082 |
| 255 | Streptomyces roseofulvus | frenolicin | acetyl, butyryl-7 | 487889 | 487890 |
| 267 | Streptomyces venezuelae ATCC 10712 | jadomycin | acetyl-9 | 510722 | 510723 |
| 271 | Streptomyces sp. | daunorubicin | propionyl-9 | 516109 | 516110 |
| 278 | Streptomyces peucetius | daunorubicin | propionyl-9 | 532245 | 532246 |
| 331 | Streptomyces fradiae | urdamycin | acetyl-9 | 809105 | 809106 |
| 350 | Streptomyces argillaceus | mithramycin | acetyl-9 | 927517 | 927518 |
| 618 | Actinomadura hibisca | pradimicin | acetyl-11 | 2580442 | 2580443 |
| 666 | Streptomyces nogalater | nogalamycin | acetyl-9 | 2916812 | 2916813 |
| 840 | Streptomyces cyanogenus | landomycin | acetyl-9 | 4240405 | 4240406 |
| 853 | Streptomyces arenae | naphthocyclinone | acetyl-7 | 4416222 | 4416223 |
| 1082 | Streptomyces rochei | | | 6518511 | 6518512 |
| 1240 | Streptomyces galilaeus | aclacinomycin | propionyl-9 | 7800665 | 7800666 |
| 1293 | Streptomyces maritimus | enterocin | benzoyl-7 | 8926190 | 8926191 |
| 1363 | Streptomyces collinus | rubromycin | acetyl-12 | 9944994 | 9944995 |
| 1372 | Streptomyces antibioticus | | | 9967595 | 9967596 |
| 1451 | Streptomyces collinus | | | 11024335 | 11024336 |
| 1462 | Streptomyces sp. R1128 | R1128 | acetyl, propionyl, isobutyryl, | 11096114 | 11096113 |
| 1602 | Streptomyces antibioticus | simocyclinone | acetyl-9 | 12744820 | 12744821 |
| 1936 | Streptomyces sp. PGA64 | | | 14280343 | 14280344 |
| 1961 | Streptomyces aureofaciens | | | 14486277 | 14486278 |
| 4053 | Streptomyces galilaeus | aclacinomycin | propionyl-9 | 16945714 | 16945715 |

TABLE 4-continued

List of ketosynthase α/β genes used to construct the dendrogram shown in FIG. 3.

| PKS_Cluster_ID | Strain name | Compound name | starter unit - number of cycles | NCBI gi Ksα | NCBI gi KSβ |
|---|---|---|---|---|---|
| 5057 | *Streptomyces* sp. JP95 | griseorhodin | acetyl-12 | 21039488 | 21039489 |
| 5194 | *Streptomyces coelicolor* A3(2) | actinorhodin | acetyl-7 | 21223458 | 21223459 |
| 5199 | *Streptomyces coelicolor* A3(2) | WhiE spore pigment | acetyl-11 | 21223681 | 21223680 |
| 7535 | *Streptomyces murayamaensis* | kinamycin | acetyl-9 | 29469233 | 29469234 |
| 7536 | *Streptomyces* sp. WP 4669 | PD 116740 | acetyl-9 | 29469252 | 29469253 |
| 7645 | *Streptomyces avermitilis* MA-4680 | | | 29828918 | 29828917 |
| 7660 | *Streptomyces avermitilis* MA-4680 | | | 29829380 | 29829381 |
| 8090 | *Streptomyces rochei* | | | 30795041 | 30795040 |
| 8177 | *Streptomyces griseoflavus* | gilvocarcin | propionyl-9 | 32140283 | 32140284 |
| 8249 | *Streptomyces* sp. AM-7161 | medermycin | acetyl-7 | 32469270 | 32469271 |
| 8376 | *Streptomyces griseoruber* | hedamycin | hexadienyl-9 | 32492544 | 32492543 |
| 9797 | *Streptomyces griseus* subsp. *griseus* | chromomycin | acetyl-9 | 40644834 | 40644833 |
| 10322 | *Streptomyces resistomycificus* | resistomycin | acetyl-9 | 45259316 | 45259317 |
| 14512 | *Streptomyces aureofaciens* | | | 61968692 | 61968693 |
| 15377 | *Streptomyces chartreusis* | chartreusin | acetyl-9 | 68146474 | 68146475 |
| 16636 | *Thermobifida fusca* YX | | | 72161622 | 72161623 |
| 19686 | *Streptomyces steffisburgensis* | steffimycin | acetyl-9 | 84619196 | 84619195 |
| 20414 | *Frankia* sp. Ccl3 | | | 86741538 | 86741537 |
| 20443 | *Frankia* sp. Ccl3 | | | 86742778 | 86742777 |
| 20676 | *Streptomyces* sp. SCC 2136 | Sch 47554 | acetyl-9 | 88319793 | 88319792 |
| 24777 | *Frankia alni* ACN14a | | | 111223784 | 111223783 |
| 29025 | *Streptomyces echinatus* | aranciamycin | acetyl-9 | 118722503 | 118722502 |
| 34741 | *Salinispora tropica* CNB-440 | lysolipin | acetyl-12 | 145595027 | 145595026 |
| 40173 | *Streptomyces tendae* | lysolipin | acetyl-12 | 154623217 | 154623216 |
| 41981 | *Streptomyces olivaceus* | elloramycin | acetyl-9 | 158148282 | 158148283 |
| 42141 | *Frankia* sp. EAN1pec | | | 158314223 | 158314224 |
| 42791 | *Salinispora arenicola* CNS-205 | | | 159038259 | 159038258 |
| 43795 | *Streptomyces rishiriensis* | lactonamycin | glycyl-9 | 161367388 | 161367389 |
| 43796 | *Streptomyces sanglieri* | lactonamycin | glycyl-9 | 161367423 | 161367424 |
| 46244 | *Streptomyces* sp. A2991200 | benastatin | hexanoyl-11 | 169402965 | 169402966 |
| 55558 | *Streptomyces* sp. CM020 | alnumycin | butyryl-7 | 209863916 | 209863917 |
| 60942 | *Streptomyces diastatochromogenes* | polyketomycin | acetyl-9 | 224812396 | 224812397 |
| 62857 | *Micromonospora* sp. Tu 6368 | saquayamycin/ galtamycin | acetyl-9 | 227121321 | 227121322 |
| 69714 | *Catenulispora acidiphila* DSM 44928 | | | 256390289 | 256390290 |
| 69785 | *Catenulispora acidiphila* DSM 44928 | | | 256392728 | 256392729 |
| 69874 | *Catenulispora acidiphila* DSM 44928 | | | 256395612 | 256395613 |
| 70552 | *Saccharomonospora viridis* DSM 43017 | | | 257057328 | 257057329 |
| 72906 | uncultured soil bacterium V167 | erdacin | acetyl-7 | 261497157 | 261497158 |
| 73636 | *Streptomyces albaduncus* | chrysomycin | propionyl-9 | 266631088 | 266631089 |
| 73727 | *Streptomyces ravidus* | ravidomycin | propionyl-9 | 268322287 | 268322286 |
| 74055 | *Thermomonospora curvata* DSM 43183 | | | 269126987 | 269126986 |
| 74963 | *Streptosporangium roseum* DSM 43021 | | | 271965601 | 271965602 |
| 75562 | *Kibdelosporangium* sp. MJ126-NF4 | azicemicin | aziridinyl-9 | 282801740 | 282801741 |
| 75659 | *Micromonospora echinospora* subsp. *challisensis* | TLN-05220/ TLN-05223 | 2-methylbutyryl-12 | 283484105 | 283484106 |
| 76636 | *Geodermatophilus obscurus* DSM 43160 | | | 284988769 | 284988768 |
| 78051 | *Streptomyces scabiei* 87.22 | | | 290958762 | 290958763 |
| 79150 | *Streptomyces flavogriseus* | xantholipin | acetyl-12 | 292386134 | 292386133 |
| 79346 | *Streptomyces* sp. SF2575 | SF2575 | malonamyl-8 | 292659136 | 292659137 |
| 80870 | *Streptomyces* sp. SANK 61196 | A-74528 | hexadienyl-12 | 296046088 | 296046089 |
| 81263 | *Cellulomonas flavigena* DSM 20109 | | | 296131162 | 296131163 |
| 81492 | *Streptomyces* sp. 2238-SVT4 | hatomarubigin | acetyl-9 | 296178419 | 296178421 |
| 82673 | *Nocardiopsis dassonvillei* subsp. *dassonvillei* DSM | | | 297563194 | 297563193 |
| 83633 | *Amycolatopsis orientalis* subsp. *vinearia* | BE-7585A | acetyl-9 | 298256334 | 298256335 |
| 85310 | *Amycolatopsis mediterranei* U32 | | | 300787306 | 300787305 |
| 85631 | uncultured soil bacterium | | | 301057030 | 301057029 |
| 87643 | *Micromonospora aurantiaca* ATCC 27029 | | | 302867962 | 302867961 |
| 87658 | *Micromonospora aurantiaca* ATCC 27029 | | | 302868481 | 302868480 |
| 90317 | *Streptomyces vietnamensis* | granaticins | acetyl-7 | 308445212 | 308445213 |
| 92367 | *Frankia* sp. Eul1c | | | 312195193 | 312195194 |
| 92480 | *Frankia* sp. Eul1c | | | 312198553 | 312198552 |
| 94033 | *Micromonospora* sp. L5 | | | 315505143 | 315505144 |
| 94047 | *Micromonospora* sp. L5 | | | 315505638 | 315505639 |
| 94215 | *Streptomyces* sp. TA-0256 | FD-594 | butyryl-12 | 316997093 | 316997094 |
| 101715 | *Verrucosispora maris* AB-18-032 | | | 330467594 | 330467593 |
| 101749 | *Verrucosispora maris* AB-18-032 | | | 330468706 | 330468705 |
| 104052 | uncultured bacterium BAC AB649/1850 | fluostatin | acetyl-9 | 332380592 | 332380591 |
| 106770 | *Frankia* symbiont of Datisca glomerata | | | 336176581 | 336176580 |
| 106811 | *Frankia* symbiont of Datisca glomerata | | | 336178278 | 336178279 |
| 106823 | *Frankia* symbiont of Datisca glomerata | | | 336178651 | 336178650 |
| 108952 | *Streptomyces aureofaciens* | chlortetracycline | malonamyl-8 | 338776764 | 338776763 |
| 112117 | uncultured bacterium | | | 343479049 | 343479050 |
| 112118 | uncultured bacterium | AZ154 | acetyl-12 | 343479100 | 343479099 |
| 112119 | uncultured bacterium | X26 | acetyl-9 | 343479142 | 343479141 |

TABLE 4-continued

List of ketosynthase α/β genes used to construct the dendrogram shown in FIG. 3.

| PKS_Cluster_ID | Strain name | Compound name | starter unit - number of cycles | NCBI gi KSα | NCBI gi KSβ |
|---|---|---|---|---|---|
| 112975 | *Streptomyces* sp. SirexAA-E | | | 344997887 | 344997886 |
| 113100 | *Streptomyces* sp. SirexAA-E | | | 345002705 | 345002706 |
| 113134 | *Streptomyces* sp. SirexAA-E | | | 345003803 | 345003804 |
| 113264 | *Streptomyces violaceusniger* Tu 4113 | | | 345010189 | 345010188 |
| 118702 | *Kitasatospora setae* KM-6054 | | | 357394114 | 357394115 |
| 119143 | *Streptomyces flavogriseus* ATCC 33331 | | | 357414496 | 357414495 |
| 119163 | *Streptomyces flavogriseus* ATCC 33331 | | | 357415186 | 357415187 |
| 123050 | *Streptomyces bingchenggensis* BCW-1 | | | 374985521 | 374985522 |
| 123163 | *Streptomyces bingchenggensis* BCW-1 | | | 374989600 | 374989601 |
| 133702 | *Streptomyces hygroscopicus* subsp. *jinggangensis* 50 | | | 386837281 | 386837280 |
| 133764 | *Streptomyces hygroscopicus* subsp. *jinggangensis* 50 | | | 386839769 | 386839768 |
| 136283 | *Modestobacter marinus* | | | 389861877 | 389861876 |
| 145596 | *Nocardiopsis alba* ATCC BAA-2165 | | | 403508105 | 403508106 |
| 148526 | *Nocardia brasiliensis* ATCC 700358 | | | 407642667 | 407642668 |
| 148574 | *Nocardia brasiliensis* ATCC 700358 | | | 407644198 | 407644199 |
| 150287 | *Dactylosporangium* sp. SC14051 | dactylocycline | malonamyl-8 | 408451285 | 408451286 |
| 150648 | *Streptomyces venezuelae* ATCC 10712 | | | 408682514 | 408682513 |
| 153658 | uncultured bacterium | tetarimycin | acetyl-9 | 426272821 | 426272820 |
| 158184 | *Saccharothrix espanaensis* DSM 44229 | | | 433607249 | 433607250 |
| 159349 | *Gloeocapsa* sp. PCC 7428 | | | 434395464 | 434395463 |
| 176862 | *Streptomyces davawensis* JCM 4913 | | | 471321947 | 471321946 |
| 176863 | *Streptomyces davawensis* JCM 4913 | | | 471321991 | 471321990 |
| 181809 | *Streptomyces* sp. PAMC26508 | | | 479318246 | 479318247 |
| 196135 | *Streptomyces fulvissimus* DSM 40593 | | | 488611453 | 488611454 |
| 212645 | *Streptomyces clavuligerus* | | | 294328345 | 294328346 |
| 213049 | *Streptomyces rimosus* | oxytetracycline | malonamyl-8 | 440620236 | 440620260 |
| 213391 | *Streptomyces viridochromogenes* | | | 302471833 | 302471834 |
| 223789 | *Streptomyces griseoflavus* | | | 302474694 | 302474695 |
| 224176 | *Streptomyces mobaraensis* | | | 453051297 | 453051296 |
| 224763 | *Streptomyces* | | | 291344118 | 291344117 |
| 227300 | *Amycolatopsis azurea* | | | 449420704 | 449420705 |
| 231513 | *Saccharomonospora azurea* | | | 359738726 | 359738725 |
| 231668 | *Saccharomonospora cyanea* | | | 374661362 | 374661363 |
| 231815 | *Saccharomonospora glauca* | | | 384521847 | 384521848 |
| 232091 | *Streptomyces bottropensis* | | | 456387833 | 456387834 |
| 232121 | *Streptomyces bottropensis* | | | 456387348 | 456387347 |
| 238702 | *Streptomyces gancidicus* | | | 455651441 | 455651440 |
| 238799 | *Streptomyces gancidicus* | | | 455647826 | 455647827 |
| 238970 | *Streptomyces griseoaurantiacus* | | | 329303135 | 329303134 |
| 240531 | *Saccharomonospora xinjiangensis* | | | 383464465 | 383464464 |
| 242194 | *Streptomyces tsukubaensis* | | | 385668968 | 385668967 |
| 242776 | *Streptomyces turgidiscabies* | | | 440283088 | 440283085 |
| 242940 | *Streptomyces turgidiscabies* | | | 440276217 | 440276216 |
| 245461 | *Frankia* sp. EUN1f | | | 288352379 | 288352380 |
| 245525 | *Frankia* sp. EUN1f | | | 288350346 | 288350347 |
| 246658 | *Streptomyces auratus* | | | 396997410 | 396997409 |
| 246748 | *Streptomyces auratus* | | | 396993109 | 396993110 |
| 253584 | *Amycolatopsis decaplanina* | | | 452952207 | 452952208 |
| 257598 | *Streptomyces* sp. C | | | 302441586 | 302441587 |
| 257759 | *Streptomyces* sp. C | | | 302448244 | 302448245 |
| 257760 | *Streptomyces* sp. C | | | 302448272 | 302448273 |
| 259648 | *Streptomyces sviceus* | | | 197711929 | 197711928 |
| 259749 | *Streptomyces coelicoflavus* | | | 371551784 | 371551785 |
| 260674 | *Actinoplanes* sp. N902-109 | | | 494685525 | 494685524 |
| 261168 | *Streptomyces* sp. W007 | | | 364006457 | 364006458 |
| 261395 | *Micromonospora lupini* | | | 385884259 | 385884258 |
| 261776 | *Streptomyces zinciresistens* | | | 345639059 | 345639058 |
| 261818 | *Streptomyces zinciresistens* | | | 345637421 | 345637420 |
| 262236 | *Frankia* sp. CN3 | | | 357077380 | 357077379 |
| 268606 | *Ktedonobacter racemifer* | | | 297547788 | 297547789 |
| 280551 | *Streptomyces* sp. Mg1 | | | 194344319 | 194344318 |
| 280703 | *Streptomyces* sp. SPB74 | | | 197695599 | 197695598 |
| 295708 | *Streptomyces himastatinicus* | | | 302459209 | 302459210 |
| 295719 | *Streptomyces himastatinicus* | | | 302459575 | 302459574 |
| 296212 | *Frankia* sp. QA3 | | | 392285106 | 392285107 |
| 296285 | *Frankia* sp. QA3 | | | 392287527 | 392287528 |
| 296361 | *Frankia* sp. QA3 | | | 392290229 | 392290230 |
| 300625 | *Streptomyces chartreusis* | | | 497734383 | 497734384 |
| 305098 | *Streptomyces acidiscabies* | | | 498039595 | 498039594 |
| 305257 | *Streptomyces acidiscabies* | | | 498045513 | 498045514 |
| 305264 | *Streptomyces acidiscabies* | | | 498045777 | 498045775 |
| 321155 | *Lachnospiraceae bacterium* 3-1 | | | 507762612 | 507762611 |
| 323979 | *Streptomyces* sp. HGB0020 | | | 512062730 | 512062729 |
| 324023 | *Streptomyces* sp. HGB0020 | | | 512060372 | 512060371 |
| 325070 | *Streptomyces* sp. HPH0547 | | | 512153434 | 512153433 |

TABLE 4-continued

List of ketosynthase α/β genes used to construct the dendrogram shown in FIG. 3.

| PKS_Cluster_ID | Strain name | Compound name | starter unit - number of cycles | NCBI gi Ksα | NCBI gi KSβ gi |
|---|---|---|---|---|---|
| 327338 | *Streptomyces lusitanus* | grincamycin | acetyl-9 | 514389165 | 514389166 |
| 327763 | *Streptomyces albulus* | | | 508092873 | 508092874 |
| 327785 | *Streptomyces albulus* | | | 508092166 | 508092165 |
| 329325 | *Streptomyces aurantiacus* | | | 514332066 | 514332067 |
| 330182 | *Actinoalloteichus spitiensis* | | | 515067606 | 515067605 |
| 333371 | *Streptomyces sulphureus* | | | 515467828 | 515467830 |
| 333481 | *Streptomyces sulphureus* | | | 515471814 | 515471813 |
| 338703 | *Streptomyces* sp. SS | | | 515806529 | 515806528 |
| 338710 | *Streptomyces* sp. SS | | | 515806720 | 515806721 |
| 343954 | *Nocardiopsis alba* | | | 516103130 | 516103129 |
| 344047 | *Nocardiopsis halophila* | | | 516106461 | 516106460 |
| 344192 | *Nocardiopsis prasina* | | | 516112287 | 516112286 |
| 344638 | *Nocardiopsis synnemataformans* | | | 516133090 | 516133089 |
| 344744 | *Nocardiopsis synnemataformans* | | | 516136652 | 516136651 |
| 344838 | *Nocardiopsis halotolerans* | | | 516140432 | 516140433 |
| 344901 | *Nocardiopsis halotolerans* | | | 516143136 | 516143135 |
| 345039 | *Nocardiopsis valliformis* | | | 516148637 | 516148638 |
| 345285 | *Nocardiopsis ganjiahuensis* | | | 516162729 | 516162731 |
| 345298 | *Nocardiopsis ganjiahuensis* | | | 516163860 | 516163858 |
| 345500 | *Nocardiopsis potens* | | | 516177487 | 516177485 |
| 345691 | *Nocardiopsis alkaliphila* | | | 516194141 | 516194140 |
| 354385 | *Streptomyces* sp. FxanaC1 | | | 516769011 | 516769013 |
| 354662 | *Streptomyces* | | | 516790530 | 516790531 |
| 354667 | *Streptomyces* | | | 516790775 | 516790772 |
| 354765 | *Streptomyces* | | | 516797526 | 516797524 |
| 359878 | *Streptomyces vitaminophilus* | | | 517194301 | 517194300 |
| 362034 | *Streptomyces* sp. CcalMP-8W | | | 517298639 | 517298640 |
| 362071 | *Streptomyces* sp. CcalMP-8W | | | 517300121 | 517300122 |
| 362751 | *Frankia* sp. BCU110501 | | | 517330197 | 517330198 |
| 363206 | *Streptomyces* | | | 517349015 | 517349014 |
| 363377 | *Streptomyces* sp. HmicA12 | | | 517356095 | 517356094 |
| 363616 | *Streptomyces* sp. MspMP-M5 | | | 517364723 | 517364724 |
| 363634 | *Streptomyces* sp. MspMP-M5 | | | 517365652 | 517365653 |
| 363678 | *Streptomyces* sp. MspMP-M5 | | | 517367650 | 517367649 |
| 363805 | *Streptomyces* sp. LaPpAH-108 | | | 517372962 | 517372963 |
| 363824 | *Streptomyces* sp. LaPpAH-108 | | | 517373726 | 517373725 |
| 363894 | *Streptomyces* sp. ATexAB-D23 | | | 517376190 | 517376191 |
| 364010 | *Streptomyces* sp. ATexAB-D23 | | | 517380234 | 517380233 |
| 364083 | *Streptomyces* sp. BoleA5 | | | 517382660 | 517382661 |
| 364264 | *Streptomyces* sp. BoleA5 | | | 517389779 | 517389778 |
| 364368 | *Streptomyces* sp. PsTaAH-124 | | | 517393575 | 517393576 |
| 365742 | *Frankia* sp. BMG5.12 | | | 517467538 | 517467539 |
| 366519 | *Actinokineospora enzanensis* | | | 517511338 | 517511339 |
| 366522 | *Actinokineospora enzanensis* | | | 517511425 | 517511424 |
| 366523 | *Actinokineospora enzanensis* | | | 517511485 | 517511486 |
| 366530 | *Actinokineospora enzanensis* | | | 517511634 | 517511633 |
| 366587 | *Actinokineospora enzanensis* | | | 517513802 | 517513801 |
| 367271 | *Salinispora pacifica* | | | 517549947 | 517549948 |
| 367321 | *Salinispora pacifica* | | | 517552055 | 517552054 |
| 367380 | *Salinispora pacifica* | | | 517554571 | 517554572 |
| 367531 | *Salinispora pacifica* | | | 517560266 | 517560265 |
| 367614 | *Salinispora pacifica* | | | 517563182 | 517563181 |
| 367702 | *Salinispora pacifica* | | | 517566341 | 517566340 |
| 367758 | *Salinispora pacifica* | | | 517568116 | 517568115 |
| 367938 | *Salinispora pacifica* | | | 517574884 | 517574885 |
| 367951 | *Salinispora pacifica* | | | 517575473 | 517575472 |
| 368772 | *Micromonospora* sp. CNB394 | | | 517613873 | 517613874 |
| 368863 | *Micromonospora* sp. CNB394 | | | 517617890 | 517617891 |
| 369056 | *Salinispora arenicola* | | | 517624668 | 517624667 |
| 369191 | *Salinispora arenicola* | | | 517629449 | 517629450 |
| 369636 | *Salinispora pacifica* | | | 517644688 | 517644689 |
| 369704 | *Salinispora pacifica* | | | 517647314 | 517647315 |
| 369787 | *Salinispora pacifica* | | | 517650873 | 517650874 |
| 369860 | *Salinispora pacifica* | | | 517653383 | 517653382 |
| 369866 | *Salinispora pacifica* | | | 517653809 | 517653808 |
| 370481 | *Streptomyces* sp. CNT372 | | | 517676353 | 517676354 |
| 372859 | *Streptomyces* sp. CNB091 | | | 517789797 | 517789796 |
| 374795 | *Streptomyces prunicolor* | | | 517891591 | 517891590 |
| 375049 | *Streptomyces* sp. R1-NS-10 | | | 517900262 | 517900263 |
| 378368 | *Streptomyces* sp. TOR3209 | | | 518156679 | 518156680 |
| 378814 | *Streptomyces* sp. AA1529 | | | 518188243 | 518188242 |
| 378859 | *Streptomyces* sp. AA1529 | | | 518189500 | 518189499 |
| 380280 | *Streptomyces* sp. AA0539 | | | 518262143 | 518262142 |
| 382025 | *Streptomyces* sp. FxanaD5 | | | 518354660 | 518354659 |
| 382069 | *Streptomyces* sp. FxanaD5 | | | 518356686 | 518356687 |

TABLE 4-continued

List of ketosynthase α/β genes used to construct the dendrogram shown in FIG. 3.

| PKS_Cluster_ID | Strain name | Compound name | starter unit - number of cycles | NCBI gi Ksα | NCBI gi KSβ gi |
|---|---|---|---|---|---|
| 382409 | *Streptomyces sulphureus* | | | 518373928 | 518373929 |
| 382423 | *Streptomyces sulphureus* | | | 518374555 | 518374554 |
| 382559 | *Streptomyces sulphureus* | | | 518379252 | 518379251 |
| 384287 | *Actinomadura atramentaria* | | | 518464803 | 518464802 |
| 393483 | *Streptomyces canus* | | | 518960103 | 518960102 |
| 393582 | *Streptomyces canus* | | | 518963441 | 518963442 |
| 393751 | *Streptomyces* sp. 303MFCol5.2 | | | 518969878 | 518969877 |
| 393912 | *Streptomyces* sp. 303MFCol5.2 | | | 518975094 | 518975095 |
| 393952 | *Streptomyces* sp. 303MFCol5.2 | | | 518976223 | 518976224 |
| 394009 | *Streptomyces* sp. 351MFTsu5.1 | | | 518978505 | 518978504 |
| 394196 | *Streptomyces* sp. 351MFTsu5.1 | | | 518985500 | 518985501 |
| 396493 | *Streptomyces afghaniensis* | | | 514936636 | 514936635 |
| 400423 | *Sciscionella marina* | | | 521986047 | 521986046 |
| 401818 | *Streptomyces scabrisporus* | | | 522042542 | 522042543 |
| 421616 | *Streptomyces collinus* Tu 365 | | | 529225472 | 529225473 |
| 421635 | *Streptomyces collinus* Tu 365 | | | 529226334 | 529226333 |
| o1 | *Streptomyces griseus* | fredericamycin | hexadienyl-12 | 33327096 | 33327097 |
| o2 | *Streptomyces violaceoruber* | granaticin | acetyl-7 | 4218564 | 4218565 |
| o3 | *Streptomyces glaucescens* | tetracenomycin | acetyl-9 | 153496 | 153497 |
| o4 | *Streptomyces olindensis* | cosmomycin | propionyl-9 | 83272129 | 83272131 |
| o5 | *Streptomyces halstedii* | Sch spore pigment | acetyl-11 | 153323 | 153324 |
| o6 | *Streptomyces griseus* | griseusin | acetyl-9 | 581665 | 581666 |

TABLE 5

List of type I polyketide, type II polyketide, and non-ribosomal peptide natural product gene clusters identified in *Frankia* genomes using DYNAMITE software. Type II polyketide clusters are in bold, and those within the diverged clade examined in this study are labeled with *** in the "Cluster type" column.

| Organism | Cluster # | First protein | Last protein | Cluster type |
|---|---|---|---|---|
| *Frankia alni* ACN14a | 1 | 111219827 | 111219853 | cis-AT_PKS-I |
| *Frankia alni* ACN14a | 2 | 111220746 | 111220752 | cis-AT_PKS-I |
| *Frankia alni* ACN14a | 3 | 111220995 | 111221007 | cis-AT_PKS-I |
| *Frankia alni* ACN14a | 4 | 111221105 | 111221124 | cis-AT_PKS-I |
| *Frankia alni* ACN14a | 5 | 111221959 | 111221990 | cis-AT_PKS-I NRPS |
| *Frankia alni* ACN14a | 6 | 111222328 | 111222337 | cis-AT_PKS-I |
| *Frankia alni* ACN14a | 7 | 111222397 | 111222407 | cis-AT_PKS-I |
| *Frankia alni* ACN14a | 8 | 111222599 | 111222615 | cis-AT_PKS-I |
| *Frankia alni* ACN14a | 9 | 111222836 | 111222874 | cis-AT_PKS-I |
| *Frankia alni* ACN14a | 10 | 111223473 | 111223488 | cis-AT_PKS-I |
| *Frankia alni* ACN14a | 11 | 111223558 | 111223561 | NRPS |
| *Frankia alni* ACN14a | 12 | 111223568 | 111223571 | NRPS |
| ***Frankia alni* ACN14a** | 13 | 111223775 | 111223796 | **PKS-II \*\*\*** |
| *Frankia* sp. BCU110501 | 1 | 517315950 | 517315964 | cis-AT_PKS-I |
| *Frankia* sp. BCU110501 | 2 | 517318311 | 517318315 | cis-AT_PKS-I |
| *Frankia* sp. BCU110501 | 3 | 517318392 | 517318395 | cis-AT_PKS-I |
| *Frankia* sp. BCU110501 | 4 | 517320080 | 517320097 | cis-AT_PKS-I |
| *Frankia* sp. BCU110501 | 5 | 517321349 | 517321351 | cis-AT_PKS-I |
| *Frankia* sp. BCU110501 | 6 | 517321360 | 517321360 | trans-AT_PKS-I |
| *Frankia* sp. BCU110501 | 7 | 517321369 | 517321369 | cis-AT_PKS-I |
| *Frankia* sp. BCU110501 | 8 | 517321380 | 517321416 | cis-AT_PKS-I |
| *Frankia* sp. BCU110501 | 9 | 517321456 | 517321482 | cis-AT_PKS-I |
| *Frankia* sp. BCU110501 | 10 | 517322903 | 517322915 | cis-AT_PKS-I |
| *Frankia* sp. BCU110501 | 11 | 517326987 | 517327012 | cis-AT_PKS-I |
| *Frankia* sp. BCU110501 | 12 | 517327259 | 517327270 | cis-AT_PKS-I |
| *Frankia* sp. BCU110501 | 13 | 517327292 | 517327301 | cis-AT_PKS-I |
| *Frankia* sp. BCU110501 | 14 | 517329256 | 517329256 | NRPS |
| *Frankia* sp. BCU110501 | 15 | 517329264 | 517329282 | cis-AT_PKS-I |
| ***Frankia* sp. BCU110501** | 16 | 517330195 | 517330199 | **PKS-II \*\*\*** |
| *Frankia* sp. BCU110501 | 17 | 517330237 | 517330238 | cis-AT_PKS-I |
| *Frankia* sp. BCU110501 | 18 | 517330542 | 517330555 | cis-AT_PKS-I |
| *Frankia* sp. BCU110501 | 19 | 517330874 | 517330877 | cis-AT_PKS-I |
| *Frankia* sp. BCU110501 | 20 | 522061021 | 522061026 | cis-AT_PKS-I |
| *Frankia* sp. BCU110501 | 21 | 522061077 | 522061102 | cis-AT_PKS-I |
| *Frankia* sp. BCU110501 | 22 | 522061305 | 522061310 | cis-AT_PKS-I |
| *Frankia* sp. BCU110501 | 23 | 522061453 | 522061455 | NRPS |
| *Frankia* sp. BMG5.12 | 1 | 517464459 | 517464497 | cis-AT_PKS-I |
| *Frankia* sp. BMG5.12 | 2 | 517464551 | 517464551 | cis-AT_PKS-I |
| *Frankia* sp. BMG5.12 | 3 | 517464741 | 517464750 | trans-AT_PKS-I |

TABLE 5-continued

List of type I polyketide, type II polyketide, and non-ribosomal peptide natural product gene clusters identified in *Frankia* genomes using DYNAMITE software. Type II polyketide clusters are in bold, and those within the diverged clade examined in this study are labeled with *** in the "Cluster type" column.

| Organism | Cluster # | Gene cluster protein ID range | | Cluster type |
|---|---|---|---|---|
| | | First protein | Last protein | |
| *Frankia* sp. BMG5.12 | 4 | 517466209 | 517466232 | cis-AT_PKS-I |
| *Frankia* sp. BMG5.12 | 5 | 517466408 | 517466427 | cis-AT_PKS-I |
| *Frankia* sp. BMG5.12 | 6 | 517467058 | 517467067 | NRPS |
| ***Frankia* sp. BMG5.12** | 7 | 517467530 | 517467551 | **PKS-II ***** |
| *Frankia* sp. BMG5.12 | 8 | 517467647 | 517467666 | cis-AT_PKS-I |
| *Frankia* sp. BMG5.12 | 9 | 517468621 | 517468636 | cis-AT_PKS-I |
| *Frankia* sp. BMG5.12 | 10 | 517468646 | 517468661 | cis-AT_PKS-I |
| *Frankia* sp. BMG5.12 | 11 | 517468751 | 517468764 | cis-AT_PKS-I |
| *Frankia* sp. BMG5.12 | 12 | 517468895 | 517468903 | NRPS |
| *Frankia* sp. BMG5.12 | 13 | 517469047 | 517469051 | cis-AT_PKS-I |
| *Frankia* sp. BMG5.12 | 14 | 517469097 | 517469112 | cis-AT_PKS-I |
| *Frankia* sp. BMG5.12 | 15 | 517469399 | 517469441 | cis-AT_PKS-I |
| *Frankia* sp. BMG5.12 | 16 | 517469491 | 517469491 | cis-AT_PKS-I |
| *Frankia* sp. BMG5.12 | 17 | 517469742 | 517469761 | cis-AT_PKS-I |
| *Frankia* sp. BMG5.12 | 18 | 517469815 | 517469815 | cis-AT_PKS-I |
| *Frankia* sp. Ccl3 | 1 | 86566498 | 86566505 | cis-AT_PKS-I |
| *Frankia* sp. Ccl3 | 2 | 86566562 | 86566566 | cis-AT_PKS-I |
| *Frankia* sp. Ccl3 | 3 | 86567541 | 86567543 | cis-AT_PKS-I NRPS |
| *Frankia* sp. Ccl3 | 4 | 86568008 | 86568019 | NRPS |
| *Frankia* sp. Ccl3 | 5 | 86568473 | 86568480 | cis-AT_PKS-I |
| *Frankia* sp. Ccl3 | 6 | 86568529 | 86568538 | cis-AT_PKS-I |
| *Frankia* sp. Ccl3 | 7 | 86739636 | 86739643 | cis-AT_PKS-I |
| *Frankia* sp. Ccl3 | 8 | 86739700 | 86739704 | cis-AT_PKS-I |
| *Frankia* sp. Ccl3 | 9 | 86740679 | 86740681 | cis-AT_PKS-I NRPS |
| *Frankia* sp. Ccl3 | 10 | 86741146 | 86741157 | NRPS |
| ***Frankia* sp. Ccl3** | 11 | 86741535 | 86741560 | **PKS-II ***** |
| *Frankia* sp. Ccl3 | 12 | 86741611 | 86741618 | cis-AT_PKS-I |
| *Frankia* sp. Ccl3 | 13 | 86741667 | 86741676 | cis-AT_PKS-I |
| ***Frankia* sp. Ccl3 | 14 | 86742770 | 86742782 | PKS-II** |
| *Frankia* sp. CN3 | 1 | 357070389 | 357070391 | cis-AT_PKS-I |
| *Frankia* sp. CN3 | 2 | 357072034 | 357072039 | cis-AT_PKS-I |
| *Frankia* sp. CN3 | 3 | 357076122 | 357076130 | cis-AT_PKS-I |
| *Frankia* sp. CN3 | 4 | 357076290 | 357076301 | cis-AT_PKS-I |
| ***Frankia* sp. CN3** | 5 | 357077366 | 357077423 | **PKS-II ***** |
| *Frankia* sp. CN3 | 6 | 357077906 | 357077910 | cis-AT_PKS-I |
| *Frankia* sp. CN3 | 7 | 357078885 | 357078885 | NRPS |
| *Frankia* sp. CN3 | 8 | 357080303 | 357080323 | NRPS |
| *Frankia* sp. CN3 | 9 | 357080338 | 357080369 | NRPS |
| *Frankia* sp. CN3 | 10 | 357081620 | 357081629 | cis-AT_PKS-I |
| ***Frankia* sp. EAN1pec** | 1 | 158314214 | 158314227 | **PKS-II ***** |
| *Frankia* sp. EAN1pec | 2 | 158314861 | 158314873 | NRPS |
| *Frankia* sp. EAN1pec | 3 | 158314895 | 158314896 | cis-AT_PKS-I |
| *Frankia* sp. EAN1pec | 4 | 158315159 | 158315199 | cis-AT_PKS-I |
| *Frankia* sp. EAN1pec | 5 | 158315264 | 158315282 | cis-AT_PKS-I |
| *Frankia* sp. EAN1pec | 6 | 158315408 | 158315418 | cis-AT_PKS-I |
| *Frankia* sp. EAN1pec | 7 | 158315653 | 158315678 | cis-AT_PKS-I |
| *Frankia* sp. EAN1pec | 8 | 158315715 | 158315756 | cis-AT_PKS-I |
| *Frankia* sp. EAN1pec | 9 | 158316046 | 158316050 | cis-AT_PKS-I |
| *Frankia* sp. EAN1pec | 10 | 158316591 | 158316614 | cis-AT_PKS-I |
| *Frankia* sp. EAN1pec | 11 | 158317359 | 158317367 | cis-AT_PKS-I |
| *Frankia* sp. EAN1pec | 12 | 158317499 | 158317526 | cis-AT_PKS-I |
| *Frankia* sp. EAN1pec | 13 | 158317682 | 158317684 | NRPS |
| *Frankia* sp. Eul1c | 1 | 312195087 | 312195107 | cis-AT_PKS-I |
| ***Frankia* sp. Eul1c | 2 | 312195185 | 312195226 | PKS-II** |
| *Frankia* sp. Eul1c | 3 | 312195425 | 312195429 | cis-AT_PKS-I |
| *Frankia* sp. Eul1c | 4 | 312196910 | 312196923 | cis-AT_PKS-I |
| *Frankia* sp. Eul1c | 5 | 312197187 | 312197202 | cis-AT_PKS-I |
| *Frankia* sp. Eul1c | 6 | 312198053 | 312198079 | cis-AT_PKS-I |
| *Frankia* sp. Eul1c | 7 | 312198185 | 312198244 | cis-AT_PKS-I |
| *Frankia* sp. Eul1c | 8 | 312198325 | 312198337 | NRPS |
| ***Frankia* sp. Eul1c** | 9 | 312198547 | 312198562 | **PKS-II ***** |
| *Frankia* sp. EUN1f | 1 | 288344572 | 288344577 | cis-AT_PKS-I |
| *Frankia* sp. EUN1f | 2 | 288344923 | 288344924 | cis-AT_PKS-I |
| *Frankia* sp. EUN1f | 3 | 288345064 | 288345067 | cis-AT_PKS-I |
| *Frankia* sp. EUN1f | 4 | 288345844 | 288345845 | NRPS |
| *Frankia* sp. EUN1f | 5 | 288346520 | 288346540 | cis-AT_PKS-I |
| *Frankia* sp. EUN1f | 6 | 288346877 | 288346877 | cis-AT_PKS-I |
| *Frankia* sp. EUN1f | 7 | 288346991 | 288346996 | cis-AT_PKS-I |
| *Frankia* sp. EUN1f | 8 | 288348482 | 288348511 | cis-AT_PKS-I |
| *Frankia* sp. EUN1f | 9 | 288349214 | 288349220 | cis-AT_PKS-I |
| *Frankia* sp. EUN1f | 10 | 288349375 | 288349390 | cis-AT_PKS-I trans-AT_PKS-I |
| *Frankia* sp. EUN1f | 11 | 288349805 | 288349811 | trans-AT_PKS-I |

TABLE 5-continued

List of type I polyketide, type II polyketide, and non-ribosomal peptide natural product gene clusters identified in *Frankia* genomes using DYNAMITE software. Type II polyketide clusters are in bold, and those within the diverged clade examined in this study are labeled with *** in the "Cluster type" column.

| Organism | Cluster # | Gene cluster protein ID range First protein | Gene cluster protein ID range Last protein | Cluster type |
|---|---|---|---|---|
| *Frankia* sp. EUN1f | 12 | 288349955 | 288349966 | NRPS |
| *Frankia* sp. EUN1f | 13 | 288350085 | 288350089 | cis-AT_PKS-I |
| ***Frankia sp.*EUN1f | 14 | 288350336 | 288350354 | PKS-II** |
| ***Frankia sp.*EUN1f** | 15 | 288352340 | 288352390 | **PKS-II \*\*\*** |
| *Frankia* sp. QA3 | 1 | 392285059 | 392285062 | NRPS |
| ***Frankia sp.*QA3** | 2 | 392285094 | 392285116 | **PKS-II \*\*\*** |
| *Frankia* sp. QA3 | 3 | 392285611 | 392285635 | cis-AT_PKS-I |
| *Frankia* sp. QA3 | 4 | 392285841 | 392285872 | cis-AT_PKS-I |
| *Frankia* sp. QA3 | 5 | 392286572 | 392286584 | NRPS |
| ***Frankia sp.*QA3 | 6 | 392287513 | 392287543 | PKS-II** |
| *Frankia* sp. QA3 | 7 | 392287695 | 392287706 | cis-AT_PKS-I |
| *Frankia* sp. QA3 | 8 | 392287915 | 392287921 | cis-AT_PKS-I |
| *Frankia* sp. QA3 | 9 | 392288746 | 392288770 | cis-AT_PKS-I |
| ***Frankia sp.*QA3 | 10 | 392290227 | 392290257 | PKS-II** |
| *Frankia* symbiont of *Datisca glomerata* | 1 | 336176511 | 336176516 | cis-AT_PKS-I |
| ***Frankia sp.*symbiont of *Datisca glomerata* | 2 | 336176578 | 336176596 | PKS-II** |
| *Frankia* symbiont of *Datisca glomerata* | 3 | 336177342 | 336177348 | cis-AT_PKS-I |
| *Frankia* symbiont of *Datisca glomerata* | 4 | 336177905 | 336177938 | cis-AT_PKS-I |
| ***Frankia sp.*symbiont of *Datisca glomerata*** | 5 | 336178258 | 336178279 | **PKS-II \*\*\*** |
| *Frankia* symbiont of *Datisca glomerata* | 6 | 336178515 | 336178538 | cis-AT_PKS-I |
| ***Frankia sp.*symbiont of *Datisca glomerata*** | 7 | 336178649 | 336178662 | **PKS-II \*\*\*** |
| *Frankia* symbiont of *Datisca glomerata* | 8 | 336178763 | 336178784 | cis-AT_PKS-I |

TABLE 6

Information on the *Frankia* genomes analyzed as part of this study.

| Organism/Name | Accession # | WGS | # of Scaffolds | # of Genes | # of Proteins | Release Date | Status |
|---|---|---|---|---|---|---|---|
| *Frankia alni* ACN14a | NC_008278.1 | — | 1 | 6775 | 6700 | Aug. 3, 2006 | Complete |
| *Frankia* sp. BCU110501 | — | ARDT01 | 194 | 6047 | 5880 | Apr. 19, 2013 | Scaffold |
| *Frankia* sp. BMG5.12 | — | ARFH01 | 135 | 5473 | 5340 | Apr. 19, 2013 | Scaffold |
| *Frankia* sp. Ccl3 | NC_007777.1 | — | 1 | 4618 | 4499 | Feb. 6, 2006 | Complete |
| *Frankia* sp. CN3 | — | AGJN02 | 2 | 7173 | 7024 | Nov. 15, 2011 | Scaffold |
| *Frankia* sp. EAN1pec | NC_009921.1 | — | 1 | 7377 | 7191 | Oct. 10, 2007 | Complete |
| *Frankia* sp. Eul1c | NC_014666.1 | — | 1 | 7263 | 7083 | Nov. 5, 2010 | Complete |
| *Frankia* sp. EUN1f | — | ADGX01 | 396 | 8236 | 8182 | Feb. 4, 2010 | Contig |
| *Frankia* sp. QA3 | NZ_CM001489.1 | AJWA01 | 1 | 6546 | 6033 | May 8, 2012 | Chromosome |
| *Frankia* symbiont of *Datisca glomerata* | NC_015656.1 | — | 3 | 4597 | 4215 | Jun. 6, 2011 | Complete |

TABLE 7

Comparative genomic summary of *Frankia* type II polyketide gene cluster biosynthesis proteins and their homolgues in pentangular and tetracenomycin tranining set clusters.

| product | species | KSα | KSβ | ACPex, ACPp | AroCycN2 |
|---|---|---|---|---|---|
| frankiamicin | *Frankia* sp. EAN1pec | FranEAN1_2393 | FranEAN1_2394 | FranEAN1_2390 | FranEAN1_2391 |
| frankiamicin | *Frankia* sp. Ccl3 | Francci3_2851 | Francci3_2850 | Francci3_2854 | Francci3_2853 |
| frankiamicin | *Frankia alni* ACN14a | FRAAL4387 | FRAAL4386 | FRAAL4390 | FRAAL4389 |
| frankiamicin | *Frankia* sp. Eul1c | FraEul1c_4753 | FraEul1c_4752 | FraEul1c_4756 | FraEul1c_4755 |
| frankiamicin | *Frankia* sp. EUN1f | FrEUN1f DRAFT_0261 | FrEUN1f DRAFT_0262 | FrEUN1f DRAFT_0258 | FrEUN1f DRAFT_0259 |
| pradimicin | *Actinomadura hibisca* | pdmA | pdmB | pdmC | pdmD |
| rubromycin | *Streptomyces collinus* | rubA | rubB | rubC | rubF (N-terminal) |
| griseorhodin | *Streptomyces* sp. JP95 | grhA | grhB | grhC | grhT (N-terminal) |

TABLE 7-continued

Comparative genomic summary of *Frankia* type II polyketide gene cluster biosynthesis proteins and their homolgues in pentangular and tetracenomycin tranining set clusters.

| | | | | | |
|---|---|---|---|---|---|
| fredericamycin | *Streptomyces griseus* | fdmF | fdmG | fdmH | fdmI |
| benastatin | *Streptomyces* sp. A2991200 | benA | benB | benC | benH (N-terminal) |
| lysolipin | *Streptomyces tendae* | llpF | llpE | llpD | llpCI |
| A-74528 | *Streptomyces* sp. SANK 61196 | sanF | sanG | sanH | sanI |
| TLN-05220, TLN-05223 | *Micromonospora echinospora* subsp. *challisensis* | TLN-ORF18 | TLN-ORF19 | TLN-ORF20 | TLN-ORF21 |
| FD-594 | *Streptomyces* sp. TA-0256 | pnxA | pnxB | pnxC, pnxV | pnxD |
| xantholipin | *Streptomyces flavogriseus* | xanF | xanE | xanD | xanC1 |
| arixanthomycins | Uncultured bacterium | arx16 | arx17 | arx18 | arx19 |
| fasamycin (AZ154) | Uncultured bacterium | ORF23 | ORF22 | ORF21 | ORF20, ORF30 |
| lactonamycin | *Streptomyces rishiriensis* | lct31 | lct32 | lct24, lct26 | lct27 |
| lactonamycin Z | *Streptomyces sanglieri* | lcz31 | lcz32 | lcz24, lcz26 | lcz27 |
| tetracenomycin | *Streptomyces glaucescens* | tcmK | tcmL | tcmM | tcmN (N-terminal) |
| elloramycin | *Streptomyces olivaceus* | elmK | elmL | elmM | elmNI |

| product | Cyc2 | Cyc1 | ABMh | ABMi | KR |
|---|---|---|---|---|---|
| frankiamicin | FranEAN1_2392 | FranEAN1_2389 | FranEAN1_2396 | FranEAN1_2397 | FranEAN1_2395 |
| frankiamicin | Francci3_2852 | Francci3_2855 | Francci3_2848 | Francci3_2847 | Francci3_2849 |
| frankiamicin | FRAAL4388 | FRAAL4392 | FRAAL4384 | FRAAL4383 | FRAAL4385 |
| frankiamicin | FraEul1c_4754 | FraEul1c_4757 | FraEul1c_4750 | FraEul1c_4749 | FraEul1c_4751 |
| frankiamicin | FrEUN1f DRAFT_0260 | FrEUN1f DRAFT_0257 | FrEUN1f DRAFT_0264 | FrEUN1f DRAFT_0265 | FrEUN1f DRAFT_0263 |
| pradimicin | pdmL | pdmK | pdmH | pdmI | pdmG |
| rubromycin | rubD | rubE | rubH | rubT | rubG |
| griseorhodin | grhS | grhQ | grhU | grhV | grhO10, grhT (C-terminal) |
| fredericamycin | fdmE | fdmD | fdmP, fdmJ | fdmQ | fdmO |
| benastatin | benD | benE | benH | benJ | benL |
| lysolipin | llpCII | llpCIII | llpOIII | llpOII | llpZI, llpZIII |
| A-74528 | sanE | sanD | sanP, sanJ | sanQ | sanO |
| TLN-05220, TLN-05223 | TLN-ORF17 | TLN-ORF16 | TLN-ORF23 | TLN-ORF24 | TLN-ORF22, TLN-ORF14 |
| FD-594 | pnxL | pnxK | pnxH | pnxI | pnxG, pnxW |
| xantholipin | xanC2 | xanC3 | xanO7 | xanO6 | xanZ3, xanZ4 |
| arixanthomycins | arx15 | arx14 | arx22 | arx23 | arx21, arx27 |
| fasamycin (AZ154) | ORF24 | ORF19 | ORF15* | ORF16* | — |
| lactonamycin | lct30 | lct29 | lct33, lct42* | — | — |
| lactonamycin Z | lcz30 | lcz29 | lcz33* | — | — |
| tetracenomycin | tcmJ | tcmI | tcmH* | — | — |
| elloramycin | elmJ | elmI | elmH* | — | — |

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A pharmaceutical composition comprising:
    frankiamicin A; and
    a pharmaceutically acceptable carrier.

2. A method of treating a subject having, or at risk of having, a condition caused by a microbial infection treatable with frankiamicin A, the method comprising:

administering to the subject an amount of frankiamicin A effective to ameliorate at least one symptom or clinical sign of the condition.

3. The method of claim 2 wherein the microbial infection comprises infection by a member of the family Staphylococcaceae.

4. The method of claim 3 wherein the member of the family Staphylococcaceae comprises *Staphylococcus aureus*.

5. The method of claim 4 wherein the *Staphylococcus aureus* comprises methicillin-resistant *S. aureus*.

* * * * *